(12) United States Patent
Kurisawa et al.

(10) Patent No.: US 10,716,959 B2
(45) Date of Patent: Jul. 21, 2020

(54) POLYMER-FLAVONOID CONJUGATES AND HYDROGELS FOR BIOMEDICAL APPLICATIONS

(71) Applicant: AGENCY FOR SCIENCE, TECHNOLOGY AND RESEARCH, Singapore (SG)

(72) Inventors: Motoichi Kurisawa, Singapore (SG); Ki Hyun Bae, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 246 days.

(21) Appl. No.: 14/916,559

(22) PCT Filed: Sep. 1, 2014

(86) PCT No.: PCT/SG2014/000412
§ 371 (c)(1),
(2) Date: Mar. 3, 2016

(87) PCT Pub. No.: WO2015/034436
PCT Pub. Date: Mar. 12, 2015

(65) Prior Publication Data
US 2016/0213787 A1    Jul. 28, 2016

(30) Foreign Application Priority Data
Sep. 3, 2013  (SG) ............................. 201306644-4

(51) Int. Cl.
| | | |
|---|---|---|
| *A61K 47/48* | (2006.01) | |
| *A61K 9/06* | (2006.01) | |
| *A61K 8/73* | (2006.01) | |
| *A61K 8/49* | (2006.01) | |
| *A61K 9/00* | (2006.01) | |
| *A61K 31/353* | (2006.01) | |
| *A61K 8/04* | (2006.01) | |
| *A61Q 19/00* | (2006.01) | |
| *C07D 311/32* | (2006.01) | |
| *A61K 8/81* | (2006.01) | |
| *A61K 47/61* | (2017.01) | |
| *A61K 47/36* | (2006.01) | |
| *A61K 47/32* | (2006.01) | |

(52) U.S. Cl.
CPC .............. *A61Q 19/00* (2013.01); *A61K 8/042* (2013.01); *A61K 8/498* (2013.01); *A61K 8/735* (2013.01); *A61K 8/8147* (2013.01); *A61K 9/0019* (2013.01); *A61K 9/06* (2013.01); *A61K 31/353* (2013.01); *A61K 47/61* (2017.08); *C07D 311/32* (2013.01); *A61K 47/32* (2013.01); *A61K 47/36* (2013.01); *A61K 2800/57* (2013.01); *A61K 2800/91* (2013.01)

(58) Field of Classification Search
CPC ...... A61K 31/353; A61K 8/498; A61K 8/735; A61K 8/8147; A61K 8/042; A61K 47/61; A61K 2000/57; A61K 2000/91; A61Q 19/00

USPC .......................................................... 514/54
See application file for complete search history.

(56) References Cited

U.S. PATENT DOCUMENTS

| | | | |
|---|---|---|---|
| 2004/0077711 A1 | 4/2004 | Torres Simon | |
| 2008/0102052 A1 | 5/2008 | Chung et al. | |

FOREIGN PATENT DOCUMENTS

| | | | | |
|---|---|---|---|---|
| CN | 101180319 A | 5/2008 | | |
| CN | 101909655 A | 12/2010 | | |
| EP | 1 352 905 A1 | 10/2003 | | |
| JP | 2009528080 A | 8/2009 | | |
| JP | 2011500799 A | 1/2011 | | |
| JP | 2012528150 A | 11/2012 | | |
| JP | 2013501781 A | 1/2013 | | |
| JP | 2013522189 A | 6/2013 | | |
| JP | 2017515834 A | 6/2017 | | |
| JP | 2017518280 A | 7/2017 | | |
| KR | 20040006955 A | 1/2004 | | |
| WO | WO00/74662 A2 | * 12/2000 | ............. | A61K 31/00 |
| WO | WO 2003/080593 A1 | 10/2003 | | |
| WO | WO 2006/124000 A1 | * 11/2006 | ............. | C08B 37/08 |
| WO | WO2006/124000 A1 | * 11/2006 | ............. | C08B 37/08 |
| WO | WO 2013/063086 A1 | * 11/2006 | ............. | A61K 39/00 |
| WO | WO 2010/138082 A1 | 12/2010 | | |
| WO | WO 2013/063086 A1 | * 5/2013 | ............. | A61K 39/00 |
| WO | WO 2015/171079 A1 | 11/2015 | | |
| WO | WO 2015/174934 A1 | 11/2015 | | |

OTHER PUBLICATIONS

Kafedjiiski et al, International Journal of Pharmaceutics, 2007, 343, 48-48.*
Lee, et al, Biomaterials, 2008, 29, 4709-4718.*
The State IP Office of China, "First Office Action," for Chinese Patent Application No. 2010480057766.1, Mar. 30, 2017, 14 pgs., Beijing, CN.
IP Office of Singapore; Search Report and the Written Opinion of Singapore Application No. 11201601612U, 11pgs. (Apr. 7, 2017).
European Patent Office, "Extended European Search Report," for European Patent Application No. 14842486.0, dated Mar. 7, 2017, 14 pgs., Munich, DE.

(Continued)

*Primary Examiner* — Ganapathy Krishnan
(74) *Attorney, Agent, or Firm* — Womble Bond Dickinson (US) LLP

(57) ABSTRACT

There is provided polymer-flavonoid conjugates. Flavonoid-grafted and flavonoid-terminated polymer conjugates are disclosed according to the invention. The linkage of flavonoids to the polymers has been achieved via thiol linkages. The inventive processes allow for making of the conjugates in high yield avoiding complex purification steps. The conjugates can be easily autoxidized to hydrogels with uses in many biomedical applications where a higher stability of the flavonoid is necessary. The hydrogels can be potentially used as viscosupplement, anti-adhesion film or dermal filler.

16 Claims, 11 Drawing Sheets

(56) References Cited

OTHER PUBLICATIONS

Kurisawa, M et al., "Injectable biodegradable hydrogels composed of hyaluronic acid-tyramine conjugates for drug delivery and tissue engineering," Chemical Communications—CHEMCOM, Jul. 28, 2005, pp. 4312-4314.

Muzolf-Panek et al., Role of Catechin Quinones in the Induction of EpRE-Mediated Gene Expression, Chemical Research in Toxicology, vol. 1, 21, No. 12, Dec. 15, 2008, pp. 2352-2360.

Unnadkat et al., "Oxidative Stability of (-)-Epigallocatechin Gallate in the Presence of Thiols," Journal of Agricultural and Food Chemistry, US, (Oct. 31, 2012), vol. 60, No. 43, pp. 10815-10821.

Peng, H. et al., Thiol Reactive Probes and Chemosensors. *Sensors*, 19, Nov. 2012, vol. 12, No. 11, pp. 15907-15946.

Sang et al., "Synthesis and Structure Identification of Thi-01 Conjugates of (-)-Epigallocatechin Gallate and Their Urinary Levels in Mice+," Chemical Research in Toxicology, vol. 18, No. 11, Nov. 1, 2005, pp. 1762-1789.

Yasuda U et al: "Deodorizing Mechanism of (-)-Epigallocatechin Gallate Against Methyl Mercaptan," Bioscience Biotechnology Biochemistry, Japan Society for Bioscience, Biotechnology, and Agrochemistry, vol. 59, No. 7, Jul. 1, 1995, pp. 1232-1236; Tokyo, Japan.

Hyukjin Lee, et al., "Synthesis, characterization, and in vivo diagnostic application of hyaluronic acid immobilized golf nanoprobes," Biomaterials, vol. 29, pp. 4709-4718 (2008).

F. Lee, et al., "An injectable enzymatically crosslinked hyaluronic acid-tyramine hydrogel system with independent tuning of mechanical strength and gelation rate," Soft Matter, Issue 4, pp. 880-887 (2008).

Joan Louise Bushman, "Green tea and cancer in humans: A review of the literature," Nutrition and Cancer, vol. 31, Issue 3, pp. 151-159 (Jan. 1998).

G.I. Ellman, "A colorimetric method for determining low concentrations of mercaptans," Archives of Biochemistry and Biophyscs, vol. 74, No. 2, pp. 443-450 (1958).

Yu Wang, et al., "Polyphenolic Chemistry of Tea and Coffee: A Century of Progress," J. Agric. Food Chem., vol. 57, No. 18, pp. 8109-8114 (2009).

PCT Notification of Transmittal of the International Search Report and the Written Opinion of the International Searching Authority, or the Declaration for counterpart PCT Application No. PCT/SG2014/000412, 12 pages, (dated Nov. 28, 2014).

Taiki Mori, et al., "Covalent Binding of Tea Catechins to Protein Thiols: The Relationship between Stability and Electrophilic Reactivity", Biosci. Biotechnol. Biochem., vol. 74, No. 12, pp. 2451-2456, (2010).

Chen, et al., "Functions of hyaluronan in wound repair," Wound Repair and Regeneration, Mar. 1999, pp. 79-89, vol. 7, No. 2.

Galati, et al., "Cellular and in vivo hepatotoxicity caused by green tea phenolic acids and catechins," Free Radical Biology & Medicine, 2006. pp. 570-580, vol. 40, Elsevier.

Ishizu, et al., "Diastereomeric difference of inclusion modes between (-)-epicatechin gallate, (-)-epigallocatechin gallate and (+)-gallocatechin gallate, with β-cyclodextrin in aqueous solvent." Magnetic Resonance in Chemistry, 2008, pp. 448-456, vol. 46, John Wiley & Sons, Ltd.

Kurisawa, et al., "Injectable enzymatically crosslinked hydrogel system with independent tuning of mechanical strength and gelation rate for drug delivery and tissue engineering," Journal of Materials Chemistry, 2010, pp. 5371-5375, No. 20, The Royal Society of Chemistry.

Laurent, et al., "Hyaluronan," The FASEB Journal, Apr. 1992, pp. 2397-2404, vol. 6.

Markman, et al., "Maillard-conjugate based core-shell co-assemblies for nanoencapsulation of hydrophobic nutraceuticals in clear beverages," Food & Function, 2012, pp. 262-270, vol. 3, The Royal Society of Chemistry.

Mizooku, et al., "Analysis of oxidized epigallocatechin gallate by liquid chromatography/mass spectrometry," Rapid Communications in Mass Spectrometry, 2003, pp. 1915-1918, vol. 17.

Moon, et al., "Synthesis, Structure Analyses, and Characterization of Novel Epigallocatechin Gallate (EGCG) Glycosides Using the Glucansucrase from Leuconostoc mesenteroides B-1299CB," Journal of Agricultural and Food Chemistry, 2006, pp. 1230-1237, vol. 54, American Chemical Society.

Sang, et al., "Stability of Tea Polyphenol (-)-Epigallocatechin-3-gallate and Formation of Dimers and Epimers under Common Experimental Conditions," Journal of Agricultural and Food Chemistry, 2005, pp. 9478-9484, vol. 53, American Chemical Society.

Schatz, et al., "Polysaccharide-Containing Block Copolymers: Synthesis, Properties and Applications of an Emerging Family of Glycoconjugates," Macromolecular Rapid Communications, 2010, pp. 1664-1684, vol. 31.

Teixeira, et al., "Enzyme-catalyzed crosslinkable hydrogels: Emerging strategies for tissue engineering," Biomaterials, 2012, pp. 1281-1290, vol. 33, Elsevier.

The First Japanese Office Action for Application No. 2016-540854 dated Mar. 20, 2018, 8 pages, (English Translation).

Tipoe, et al., "Epigallocatechin-3-gallate (EGCG) reduces liver inflammation, oxidative stress and fibrosis in carbon tetrachloride (CC14)-induced liver injury in mice," Toxicology, 2010, pp. 45-52, vol. 273, Elsevier.

Zaveri, et al., "Green tea and its polyphenolic catechins: Medicinal uses in cancer and noncancer applications," Life Sciences, 2006, pp. 2073-2080, vol. 78, Elsevier.

Zheng, et al., "Cardioprotective effects of epigallocatechin-3-gallate against doxorubicin-induced cardiomyocyte injury," European Journal of Pharmacology, 2011, pp. 82-88, vol. 652, Elsevier.

Zhu, et al., "Antioxidant Chemistry of Green Tea Catechins: Oxidation Products of (-)-Epigallocatechin Gallate and (-)-Epigallocatechin with Peroxidase," Journal of Food Lipids, 2000, pp. 275-282, vol. 7, Food & Nutrition Press, Inc., Trumbull, Connecticut.

Lowe, et al., "Thiol-X Chemistries in Polymer and Materials Science," 2013, 317 pgs., RSC Publishing.

Akagawa, et al., "Production of Hydrogen Peroxide by Polyphenols and Polyphenol-rich Beverages under Quasi-physiological Conditions," Bioscience, Biotechnology, and Biochemistry, 2003, pp. 2632-2640, vol. 67. No. 12.

Burdick, et al., "Controlled Degradation and Mechanical Behavior of Photopolymerized Hyaluronic Acid Networks," Biomacromolecules, 2005, pp. 386-391, vol. 6, No. 1.

Dube, et al., "Effective use of reducing agents and nanoparticle encapsulation in stabilizing catechins in alkaline solution," Food Chemistry, 2010, pp. 662-667, vol. 122.

Giandomenico, et al., "The Importance of Sodium Pyruvate in Assessing Damage Produced by Hydrogen Peroxide," Free Radical Biology & Medicine, 1997, pp. 426-434, vol. 23, No. 3, Elsevier Science Inc.

Hong, et al., "Stability, Cellular Uptake, Biotransformation, and Efflux of Tea Polyphenol (-)-Epigallocatechin-3-Gallate in HT-29 Human Colon Adenocarcinoma Cells," Cancer Research, Dec. 15, 2002, pp. 7241-7246, vol. 62.

Hou, et al., "Mechanism of Action of (-)-Epigallocatechin-3-Gallate: Auto-oxidation-Dependent Inactivation of Epidermal Growth Factor Receptor and Direct Effects on Growth Inhibition in Human Esophageal Cancer KYSE 150 Cells," Cancer Research, 2005, 9 pgs., vol. 65, No. 17, American Association for Cancer Research.

Ishii, et al., "Covalent modification of proteins by green tea polyphenol (-)-epigallocatechin-3-gallate through autoxidation," Free Radical Biology & Medicine, 2008, pp. 1384-1394, vol. 45, Elsevier.

Kanwar, et al., "Recent advances on tea polyphenols," Frontiers in Bioscience Elite Edition, 2012, pp. 111-131, vol. 4, National Institutes of Health.

Lambert, et al., "N-Acetylcysteine enhances the lung cancer inhibitory effect of epigallocatechin-3-gallate and forms a new adduct," Free Radical Biology & Medicine, 2008, pp. 1069-1074, vol. 44, Elsevier.

Lambert, et al., "Anticancer and Anti-inflammatory Effects of Cysteine metabolites of the Green Tea Polyphenol, (-)-epigallocatechin-

(56) References Cited

OTHER PUBLICATIONS 3-gallate," Journal of Agricultural and Food Chemistry, Sep. 22, 2010. pp. 10016-10019, vol. 58, No. 18, National Institutes of Health.

Leach, et al., "Development of photocrosslinkable hyaluronic acid-polyethylene glycol-peptide composite hydrogels for soft tissue engineering," Wiley Interscience, 2004, 9 pgs., Wiley Periodicals, Inc.

Lee, et al., "An injectable hyaluronic acid-tyramine hydrogel system for protein delivery," Journal of Controlled Release, 2009, pp. 186-193, vol. 134, Elsevier.

Li, et al., "Oxidative coupling of the pyrogallol B-ring with a galloyl group during enzymatic oxidation of epigallocatechin 3-0-gallate," Phytochemistry, 2007, pp. 1081-1088, vol. 68, Elsevier.

Mochizuki, et al., "Kinetic analysis and mechanistic aspects of autoxidation of catechins," Biochimica et Biophysica Acta, 2002, pp. 35-44, vol. 1569, Elsevier.

Onoue, et al., "Development of (-)-epigallocatechin-3-gallate (EGCG)-loaded enteric microparticles with intestinal rnucoadhesive property," International Journal of Pharmaceutics, 2011, pp. 111-113, vol. 410, Elsevier.

Sang, et al., "Autoxidative quinone formation in vitro and metabolite formation in vivo from tea polyphenol (-)-epigallocatechin-3-gallate: Studied by real-time mass spectrometry combined with tandem mass ion mapping." Free Radical Biology & Medicine, 2007, pp. 362-371, vol. 43, Elsevier.

Spencer, et al., Metabolism of Tea Flavonoids in the Gastrointestinal Tract, Proceedings of the Third International Scientific Symposium on Tea and Human Health: Role of Flavonoids in the Diet, 2003, 7 pgs., American Society for Nutritional Sciences.

The International Preliminary Report on Patentability for PCT Application No. PCT/SG2014/000412 dated Jan. 7, 2016, 25 pages.

Thomas, et al., "Aging and oxidation of reactive protein sulfhydryls," Experimental Gerontology, 2001, pp. 1519-1526, vol. 36, Elsevier.

Toole, et al., "Hyaluronan in morphogenesis," Cell & Developmental Biology, 2001, pp. 79-87, vol. 12, Academic Press.

Wong, et al., "Chapter 10: Preparation of Enzyme Immunoconjugates and other Immunoassay Components," Chemistry of Protein Conjugation and Cross-Linking, Jun. 18, 1991, 40 pages, CRC Press.

Yang, et al., "Cancer prevention by tea: animal studies, molecular mechanisms and human relevance," Nature Reviews Cancer, 2009, pp. 429-439, vol. 9, No. 6, National Institutes of Health.

Yoshioka, et al., "Formation of Radicals and Chemiluminescence during the Autoxidation of Tea Catechins," Agricultural and Biological Chemistry, 1991, pp. 2717-2723, vol. 55, No. 11.

Office action dated Mar. 20, 2018 for Japanese patent appln. No. 2016-540854.

\* cited by examiner

POLYMER-FLAVONOID CONJUGATES AND HYDROGELS FOR BIOMEDICAL APPLICATIONS

CROSS-REFERENCE TO RELATED APPLICATIONS

This patent application is a U.S. National Phase Application under 35 U.S.C. § 371 of International Application No. PCT/SG2014/000412, filed Sep. 1, 2014, entitled POLYMER-FLAVONOID CONJUGATES AND HYDROGELS FOR BIOMEDICAL APPLICATIONS, which claims priority to Singapore Patent Application No. 201306644-4, filed Sep. 3, 2013.

TECHNICAL FIELD

The present invention generally relates to a polymer-flavonoid conjugate, wherein said polymer is conjugated to said flavonoid via a thiol linker. The present invention also relates to the processes of making the conjugates as well as hydrogels comprising them and processes for making and using the hydrogels in biomedical applications.

BACKGROUND

Flavonoids have been shown to have a wide range of biological and pharmacological activities in in vitro studies. Examples include anti-allergic, anti-inflammatory, antioxidant, anti-microbial, antibacterial, antifungal, antiviral, anti-cancer, and anti-diarrheal activities. Over the past decades, for instance green tea catechins have received significant attention as protective agents against coronary heart diseases and cancers (Bushman, J. L. Green tea and cancer in humans: a review of the literature. Nutr. Cancer 31:151-9; 1998 and Zaveri, N. T. Green tea and its polyphenolic catechins: medicinal uses in cancer and noncancer applications. Life Sci. 78:2073-80; 2006). Green tea catechins belong to the group of flavonoids.

Particularly, (−)-epigallocatechin-3-gallate (EGCG) is the most abundant catechin in green tea and has been extensively studied because of its strong antioxidant and radical scavenging activity (Wang Y.; Ho C.-T. Polyphenolic Chemistry of Tea and Coffee: A Century of Progress. J Agric Food Chem 57: 8109-8114; 2009).

In spite of these desirable properties, clinical use of flavonoids, such as EGCG, has been restricted by their poor stability and limited oral bioavailability. For example, EGCG is unstable at physiological temperature and pH, and readily decomposed with a half-life of less than 30 min. Moreover, the oral bioavailability of EGCG is poor because of its rapid hydrolysis in gastric fluid and metabolic degradation in the gastrointestinal tract. To overcome the limitations, many efforts have been devoted to chemical modification of flavonoids to enhance their stability, bioavailability and biological activities.

Recently, EGCG has been covalently modified with various types of thiol-containing compounds, such as cysteine, glutathione, and proteins, but it is quite challenging to synthesize complex thiol conjugates of EGCG in a controlled manner. One important reason is chemical instability of EGCG. For instance, EGCG readily undergoes autoxidation in neutral and alkaline solution, resulting in dimerization and decomposition.

Moreover, epimerization of EGCG to (−)-gallocatechin gallate (GCG) tends to increase if the autoxidation of EGCG is inhibited by adding superoxide dismutase or by flushing with nitrogen gas. Covalent attachment of thiols to EGCG can also be hampered, by hydrogen peroxide ($H_2O_2$) generated during the autoxidation process. Since $H_2O_2$ oxidizes free thiol groups to disulphide bonds or sulfenic acids (R—SOH), it can decrease the concentration of free thiol groups that participates in thiol-EGCG conjugation. This leads to low yields and undesired, unreactive disulphide or sulfenic acid by-products in the reactions to make thiol conjugates. A complicated purification step is then necessary to obtain the desired conjugates in high yield and purity.

There is therefore a need to find an effective way to modify flavonoids, such as EGCG, with thiol-containing compounds in a highly selective manner.

Furthermore, there is currently also no way to make stable polymer-flavonoid conjugates. There is however a need to create such conjugates in order to improve the poor stability of the flavonoids and make them available in biomedical applications, such as gels.

SUMMARY

According to a first aspect, there is provided a polymer-flavonoid conjugate, wherein said polymer is conjugated to said flavonoid via a thiol linker.

Advantageously, the conjugates link the polymer in a stable way to the flavonoid moiety via a thiol link. It is possible to obtain flavonoid-terminated polymers and flavonoid-grafted polymers with improved bioavailability and bioactivity of the flavonoid.

Further advantageously, the conjugation to biocompatible and biodegradable polymers was achieved which has a potential use in biomedical applications.

According to a second aspect, there is provided a process for forming a polymer-flavonoid conjugate comprising the step of conjugating said flavonoid with said polymer via nucleophilic addition under basic conditions, wherein said polymer has been modified with a free thiol group.

Advantageously, the disclosed process allows for the reaction with very high degrees of conjugation which avoids cumbersome separation processes. The thiol conjugation can be achieved at specific points of the flavonoid structure using the disclosed process.

According to a third aspect, there is a provided a hydrogel comprising a polymer-flavonoid conjugate, wherein said polymer is conjugated to said flavonoid via a thiol linker.

Advantageously, the hydrogels could be made by the simple crosslinking of the flavonoid moieties of the disclosed conjugates, particularly when autoxidation or enzymatic crosslinking reactions are employed. The obtained hydrogels have a good storage modulus of more than about 200 pascal, often even more than 390 pascal.

According to a fourth aspect, there is therefore disclosed a process for forming a hydrogel comprising the step of cross-linking a polymer-flavonoid conjugate according to the invention via autoxidation under basic conditions. This is optionally accelerated by adding an enzyme and oxidant.

According to a fifth aspect, there is provided the use of the disclosed hydrogels for making biomedical products.

Advantageously, the hydrogels can be used in injectable hydrogel systems which provide an effective and convenient way to administer a variety of bioactive and therapeutic agents for diverse biomedical applications by choosing the flavonoid moiety and the polymer type in the conjugates as needed.

Definitions

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

Unless the context requires otherwise or specifically stated to the contrary, integers, steps, or elements of the invention recited herein as singular integers, steps or elements clearly encompass both singular and plural forms of the recited integers, steps or elements.

As used herein, unless otherwise specified, the following terms have the following meanings, and unless otherwise specified, the definitions of each term apply when that term is used individually or as a component of another term (e.g., the definition of aryl is the same for aryl and for the aryl portion of arylalkyl, alkylaryl, arylalkynyl, and the like).

As used herein, the term "flavonoid" refers to a broad class of plant secondary metabolites including without limitation the typical flavonoids (also named bioflavonoids), isoflavonoids, derived from a 3-phenylchromen-4-one (3-phenyl-1,4-benzopyrone) structure, neoflavonoids, derived from a 4-phenylcoumarine (4-phenyl-1,2-benzopyrone) structure and similar polyphenolic compounds as well as mixtures thereof. Typically, flavonoids belong to, for example, the group of flavones, flavonols, flavanones, flavanonols, flavans, proanthocyanidins and anthocyanidins. Typically, isoflavonoids belong to, for example, the group of isoflavanes, isoflavandiols, isoflavenes, coumestans and pterocarpans. Some polyphenolic compounds that can be mentioned are mesquitol and robinetinidol, ellagitannin, gallotannin, oolongtheanin, phlorotannin, tannin, theacitrin, theadibenzotropolone, theaflavin, theanaphthoquinone, thearubigins, theasinensin.

As used herein, the term "conjugate" refers to a moiety formed by the union of two compounds or a moiety united with another moiety. According to the invention the conjugation is by a covalent chemical bond via a sulfur atom.

The term "amide" as used herein refers to groups of the form —C(O)—NR$_a$-alkyl- wherein R$_a$ is selected from the group including but not limited to hydrogen, optionally substituted alkyl, optionally substituted alkenyl, and optionally substituted aryl groups. The term "amine" as used herein refers to groups of the form —NR$_a$R$_b$-alkyl- wherein R$_a$ and R$_b$ are individually selected from the group including but not limited to hydrogen, optionally substituted alkyl, optionally substituted alkenyl, and optionally substituted aryl groups. The -alkyl- groups in the "amide" and "amine" can be optionally substituted and preferably have 2 to 10 carbon atoms, more preferably 2 to 6 carbon atoms and most preferred 2 carbon atoms.

As used herein, the term "alkyl" includes within its meaning divalent ("alkylene") straight chain or branched chain saturated aliphatic groups having from 1 to 10 carbon atoms, e.g., 1, 2, 3, 4, 5, 6, 7, 8, 9, or carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like. The term "alkenyl group" includes within its meaning divalent ("alkenylene") straight or branched chain unsaturated aliphatic hydrocarbon groups having from 2 to 10 carbon atoms, e.g., 2, 3, 4, 5, 6, 7, 8, 9, or 10 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptenyl, 3-heptenyl, 1-octenyl, 1-nonenyl, 1-decenyl, and the like. The term "aryl", as used herein refers to divalent ("arylene") single, polynuclear, conjugated or fused residues of aromatic hydrocarbons having from 6 to 10 carbon atoms. Such groups include, for example, phenyl, biphenyl, naphthyl, phenanthrenyl, and the like. Aryl groups may be optionally substituted. The term "ester" includes within its meaning —O—C(O)-alkyl- and -c(O)—O-alkyl- groups. The term "carbonate" includes within its meaning —O—C(O)—O—alkyl- groups. The term "ether" includes within its meaning —O-alkyl- and -alkyl-O-alkyl- groups. The term "carbamate" includes within its meaning —O—(CO)—NR$_a$— and —O—(CO)—NR$_a$-alkyl- groups wherein R$_a$ is selected from the group including but not limited to hydrogen, optionally substituted alkyl, optionally substituted alkenyl, and optionally substituted aryl groups. The term "acetal" includes within its meaning —O—C(O-alkyl,O-alkyl)- and —O—C(O-alkyl,O-alkyl)-alkyl- groups.

The term "optionally substituted" as used herein means the group to which this term refers may be unsubstituted, or may be substituted with one or more groups independently selected from alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, alkylheteroaryl, cyano, cyanate, isocyanate, —C(O)NH(alkyl), and —C(O)N(alkyl)$_2$. Usually these groups have 1 to 10 carbon atoms, if they contain carbon atoms.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DESCRIPTION OF THE DISCLOSURE

In one aspect, there is provided a polymer-flavonoid conjugate, wherein said polymer is conjugated to said flavonoid via a thiol linker.

According to a preferred embodiment, the polymer can be selected from the group consisting of polysaccharides, polynucleotides, polypeptides, synthetic polymers and mixtures thereof. As preferred polysaccharides there can be mentioned hyaluronic acid, dextran, cellulose, amylose, starch, gelatin, alginate, chitosan, carrageenan, cyclodextrin, dextran sulfate, ficoll, gellan, guar gum, pectin, polysucrose, pullulan, scleroglucan, xanthan and xyloglucan. Hyaluronic acid can be mentioned as especially preferred. As preferred polynucleotides there can be mentioned aptamers, DNA, small interfering RNA (siRNA), microRNA, peptide nucleic acid (PNA) and small hairpin RNA (shRNA). As preferred polypeptides there can be mentioned proteins, antibodies, antibody fragments, aptides, peptides and poly(amino acid) s. As preferred synthetic polymers there can be mentioned those polymers comprising monomers selected from the group of alkenes, ethers, carboxylic acids, imines, amides, amines, anhydrides, carbonates, esters, orthoesters and urethanes. More preferred synthetic polymers that can be further mentioned include polyacrylic acid, poly(acrylamide), poly(allylamine), polyanhydrides, poly(β-amino ester), poly (butylene succinate), polycaprolactone, polycarbonate, polydioxanone, polyethylenimine, poly(glycerol), polyglycolic acid, poly(3-hydroxypropionic acid), poly(N-(2-hydroxypropyl)methacrylamide), polylactic acid, poly(lactic-co-glycolic acid), poly(methacrylic acid), poly(ortho esters), poly(2-oxazoline), poly(sebacic acid), poly(terephthalate-co-phosphate), poly(vinyl alcohol), poly(vinylpyrrolidone) and combinations thereof. Polyacrylic acid can be mentioned as most preferred.

The polymer can be linked to a single flavonoid at its terminal end of the polymer chain (flavonoid-terminated polymer) or from at several places within the polymer backbone (flavonoid-grafted polymer). The degree of conjugation for a flavonoid-terminated polymer varies with the availability with the number of available reaction places, i.e. reductive groups. It can vary widely depending on the polymer used. The polymer used in the flavonoid-terminated polymer conjugate can be of different molecular weight, preferably in the range of about 0.1 to 1000 kDa, more preferably 0.1 to 500 kDa and most preferably 0.1 to 150 kDa.

The degree of conjugation for a flavonoid-grafted polymer can be determined by the degree of substitution of carboxyl groups to cysteamine conjugates (determined for example as the number of thiol groups per 100 repeating units of polymer). It can vary widely depending on the polymer used. Typically the number of thiol groups per 100 monomer units is between about 1 and 40, preferably about 5 to 25 and most preferably 5 to 22.

The polymer used in the flavonoid-grafted polymer conjugate can be of different molecular weight, preferably in the range of about 1 to 1000 kDa, more preferably 1 to 500 kDa and most preferably 1 to 150 kDa.

According to a preferred embodiment the polymer or flavonoid can be further bound to a therapeutic agent or conjugated to a therapeutic agent.

The therapeutic agent can be selected from the group consisting of small-molecule drugs and nanomedicines wherein the nanomedicines can be themselves selected from the group consisting of polymeric micelles, liposomes and dendrimers.

According to a preferred embodiment the flavonoid can be selected from the group consisting of flavones, isoflavones, flavans, proanthocyanidins and anthocyanidins and mixtures thereof. Particularly flavans can be mentioned as flavonoids which are selected from flavans selected from the group consisting of (−)-epicatechin, (+)-epicatechin, (−)-catechin, (+)-catechin, (−)-epicatechin gallate, (+)-epicatechin gallate, epigallocatechin, epigallocatechin gallate, fisetinidol, gallocatechin, gallocatechin gallate, mesquitol and robinetinidol, ellagitannin, gallotannin, oolongtheanin, phlorotannin, tannin, theacitrin, theadibenzotropolone, theaflavin, theanaphthoquinone, thearubigins, theasinensin and mixtures thereof. If not specifically mentioned the invention includes within its scope all isomeric forms of the compounds disclosed herein, including all diastereomeric isomers, racemates and enantiomers. Thus, flavonoids should be understood to include, for example, E, Z, cis, trans, (R), (S), (L), (D), (+) and/or (−) forms of the compounds, as appropriate in each case, if not specifically mentioned otherwise.

Thiol linker means a covalent bond via a sulfur atom introduced by reacting a thiol group.

According to a preferred embodiment the thiol linker can be a derived from thiol moiety bound to said polymer, wherein said thiol moiety is selected from the group consisting of an amide, an amine, an alkyl, an alkenyl, an aryl, an ester, a carbonate, an ether, an amido, an amido ester, a carbamate and an acetal group. This moiety links the polymer and the bridging sulfur atom. Amides and amines with a thiol group are particularly preferred for making the conjugates. Most preferably the thiol moiety is an aminoethyl thiol group (cysteamine derived).

According to the invention Hyaluronic acid (HA)-EGCG conjugates via a thiol group are particularly preferred. Especially, this method allows for efficient attachment of the polymer at the C2' position of the B ring of EGCG. Two types of hyaluronic acid (HA) conjugates of EGCG can be prepared according to the preferred embodiment: EGCG-terminated HA and EGCG-grafted HA. HA is a natural polysaccharide found abundantly in the extracellular matrix of connective tissues. It plays an important role in cell proliferation, morphogenesis, inflammation, and wound repair. HA is biocompatible and biodegradable. HA was chosen in this embodiment as a backbone polymer to be attached to EGCG. The conjugation can be EGCG-terminated or EGCG-grafted. The conjugate can therefore be Hyaluronic acid-EGCG conjugate which is selected from the group consisting of:

Formula (I)

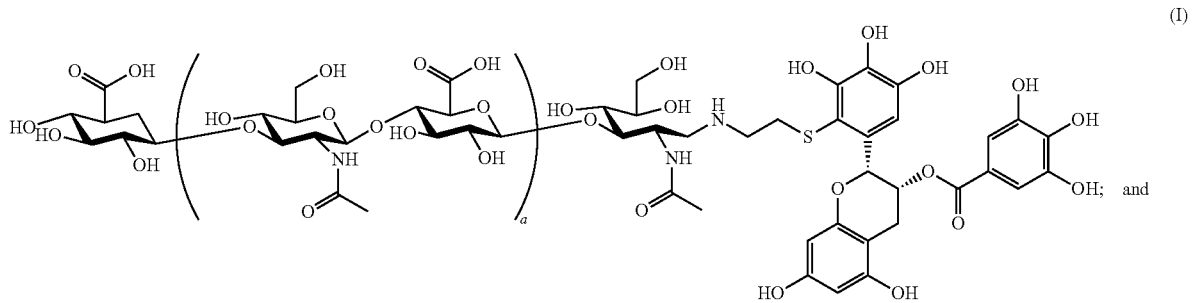

Formula (II)

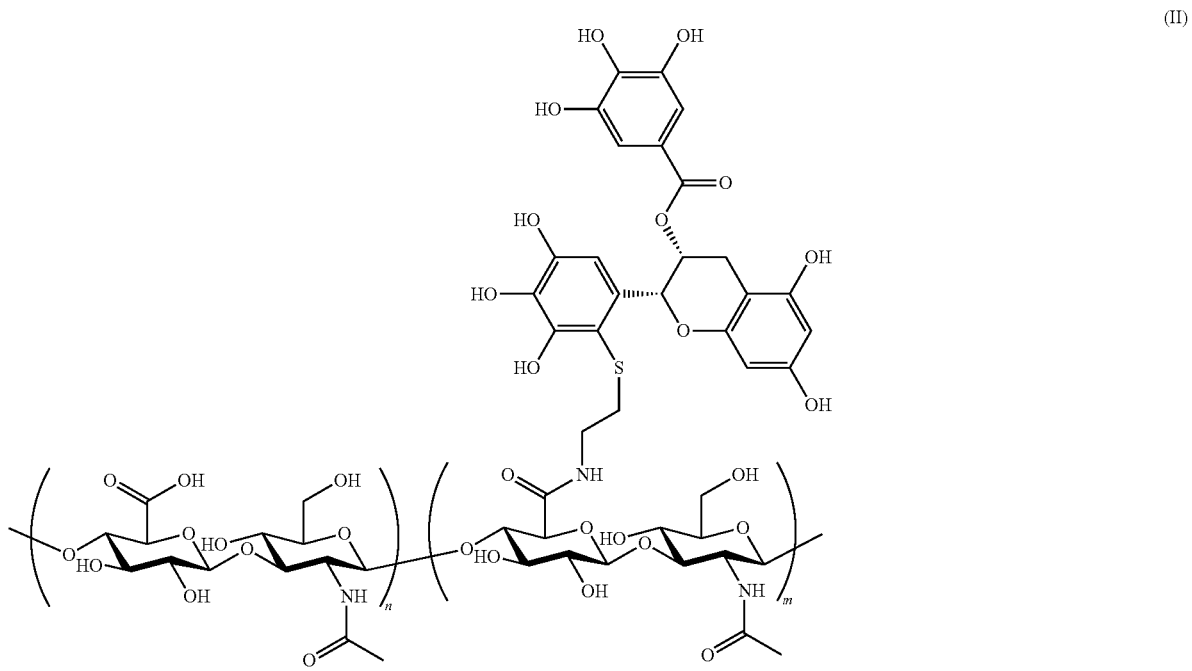

wherein:

each n is independently an integer from 0 to 15,000; and each m is independently an integer from 1 to 15,000.

Preferably n is an integer from 0 to 1,000. Preferably m is an integer from 1 to 1,000. More preferably n is an integer from 0 to 300. More preferably m is an integer from 1 to 300.

Particularly preferred are Hyaluronic acid (HA)-EGCG conjugates of the Formula (I) or (II) which have a degree of conjugation from 0.01 to 100%.

According to a second aspect, there is provided a process for forming a polymer-flavonoid conjugate comprising the step of conjugating said flavonoid with said polymer via nucleophilic addition under basic conditions, wherein said polymer has been modified with a free thiol group.

The process includes the nucleophilic reaction of the thiol group introduced in the polymer with the flavonoid. The reaction is run under basic conditions. This means that the PH is not below pH 7.0. The nucleophilic reaction can be run at high pH, but a preferred pH is pH 7.0 to 10.0 as this increases the specificity of the reaction with selected groups in the flavonoid (e.g. the galloyl group in EGCG).

Preferably the reaction is run under slightly basic condition with a pH of 7.0 to 9.0. A pH of about 7.2 to 8.2 is most preferred. Preferably a buffer, such as a phosphate buffer, is used to strictly control the reaction.

The reaction can be performed at various temperatures, but ambient temperature between 20 and 30° C. is preferred. Most preferred is about 25° C. The choice of solvent can be varied. It is preferred to run the reaction in an aqueous solvent, optionally in admixture with an organic solvent, such as DMSO. The conjugating step is preferably undertaken at a reaction time of between 1 to 36 hours, more preferably 2 to 24 hours. A reaction time of 3 to 6 hours is most preferred.

According to a preferred embodiment of the process a scavenging agent is added to the process. Said scavenging agent can be selected from the group consisting of sodium pyruvate and superoxide dismutase. Advantageously, the scavenging agent is able to efficiently scavenge undesirable $H_2O_2$ that causes side reactions. The scavenging agent, especially sodium pyruvate, can be used preferably at a concentration of 0.1 to 100 mM, more preferably 1 to 25 mM.

In the reaction the flavonoid is used preferably in excess to the thiol group carrying polymer. The excess can be 2 to 200 fold, preferably 40 to 100 fold.

According to the invention the polymer is modified with a thiol group to link to the flavonoid. According to a preferred embodiment of the invention the process comprises further the steps of:

(a) linking a thiol or disulphide containing compound to the polymer in the presence of a reducing agent; and (b) cleaving any formed disulphides at the disulphide bond to thereby form said polymer bearing a terminal thiol group.

This process is for instance suited to make flavonoid-terminated polymer conjugates. The conjugates are obtained in high purity and yields (exceeding 90%). The process is easy to run and to be scaled up. It is a non-enzymatic method with no complex purification needs.

The thiol or disulphide containing compound can be for instance be an amino alkyl thiol derivative, such as cysteamine hydrochloride and cystamine dihydrochloride.

According to a preferred embodiment the linking step (a) can be a reductive amination.

As suitable reducing agent for step (a) there can be mentioned sodium cyanoborohydride, sodium borohydride, sodium triacetoxyborohydride, lithium aluminium hydride. Particularly preferred is sodium cyanoborohydride.

The linking step (a) is preferably run under basic conditions. This means that the PH is not below pH 7.0. Preferably the reaction is run under basic condition with a pH of 7.5 to 9.0, preferably 7.5 to 8.9. A pH of about 8.5 is most preferred. Preferably a buffer, such as a borate buffer and a phosphate buffer, is used to strictly control the reaction.

The reaction of step (a) can be performed at various temperatures, but elevated temperatures between 30 and 45° C. are preferred. Most preferred is about 37° C. The choice of solvent can be varied. It is preferred to run the reaction in an aqueous solvent.

In the reaction the thiol or disulphide containing compound can be used in about equimolar amounts with the reducing agent in the corresponding reduction reaction. However, the reduction agent can also be used in excess. Usually the reaction time in step (a) can be varied in wide ranges, but it may be preferred to have long reaction times of several days, preferably 1 to 7 days, most preferred 4 to 6 days.

In the cleaving step (b) a suitable reducing agent which can cleave the disulphide bonds can be used. Such reducing agents include Tris (2-Carboxyethyl) phosphine (TCEP) or dithiothreitol (DTT). For the cleavage step the same solvents and pH may be used as in the process step (a). Reaction times are preferably 2 to 48 hours, more preferably 12 to 36 hours to achieve full cleavage. In the reduction reaction the reducing agent is used preferably in excess to the disulphide group carrying polymer. After the cleavage, purification by dialysis under nitrogen atmosphere with a given cutoff (e.g. about 1,000 to 5,000 Da) can be employed and the obtained product lyophilized for further usage in the reaction to make the final conjugates according to the invention. Thiol end modifications of more than 90% can be obtained as determined by Ellman's assay.

The polymer can also be modified with a thiol group to link to the flavonoid in other ways. According to another preferred embodiment of the invention the process for making the conjugates comprises then further the step of coupling a thiol or disulphide containing compound to said polymer in the presence of a coupling agent.

This process is for instance suited for making flavonoid-grafted polymer conjugates. The thiol or disulphide containing compound can be for instance be an amino alkyl thiol derivative, such as cysteamine hydrochloride and cystamine dihydrochloride.

The coupling agent can be a dehydration agent to activate carboxylic acids towards amide or ester formation. It can be for example selected from the group consisting of 1-ethyl-3-(3-dimethylaminopropyl)-carbodiimide hydrochloride (EDC.HCl), hydrochloride 1-ethyl-3-(3-dimethyl dicyclohexylcarbodiimide (DCC), diisopropylcarbodiimide (DIC), carbonyldiimidazole, dimethyl adipimidate, N-hydroxysuccinimide, p-nitrophenyl chloroformate and 1-(p-toluenesulfonyl)imidazole. Particularly mentioned as preferred coupling agents are also 2-Chloro-4,6-dimethoxy-1,3,5-triazine (CDMT) or 4-(4,6-Dimethoxy-1,3,5-triazin-2-yl)-4-methylmorpholinium chloride (DMTMM). To increase the stability of this active ester, N-hydroxysuccinimide (NHS) or N-hydroxysulfoxuccinimide (sulfo-NHS) can be additionally used.

The coupling step is preferably run in aqueous solution and the pH is controlled in the acidic range, e.g. of about pH 4.0 to 6.5. Preferably a nitrogen atmosphere is used for the reaction.

The coupling step can be performed at various temperatures, but ambient temperatures between 20 and 30° C. are preferred. Most preferred is about 25° C.

In the reaction the coupling agent can be used in about equimolar amounts with the COOH content of the polymer in the coupling reaction. NHS or sulfo-NHS can also be used in about equimolar amounts. Usually the reaction time in the coupling step can be varied in wide ranges, but it may be preferred to have long reaction times of several days, preferably 1 to 2 days.

As the reaction product may contain disulphide bridges a cleavage step may be used. The cleavage step may be identical or substantially identical to the cleavage step (b) described for the other process of modifiying the polymer with thiol groups. Purification can also be analogous.

According to a third aspect of the invention, there is provided a hydrogel comprising a polymer-flavonoid conjugate, wherein said polymer is conjugated to said flavonoid via a thiol linker.

A polymer-flavonoid conjugate of the Formula (II) which has a degree of conjugation from 0.01 to 100%, preferably 2 to 40%, more preferably any of the following values 2%, 5%, 7.5%, 10%, 20%, 30%, and 40% can be suitable in the hydrogel and is specifically mentioned.

According to a fourth aspect of the invention, there is disclosed a preferred process for forming a hydrogel according to the invention comprising the step of cross-linking a polymer-flavonoid conjugate via autoxidation under basic conditions.

The polymer-flavonoid conjugate is a polymer-flavonoid conjugate according to the invention as mentioned above.

The process for forming the hydrogel is preferably run under basic conditions. This means that the PH is not below pH 7.0. Preferably the reaction is run under basic condition with a pH of 7.0 to 8.0, preferably about 7.4. Preferably a buffer, such as a phosphate buffer, is used to strictly control the reaction. The coupling step can be performed at various temperatures, but elevated temperatures between 30 and 40° C. are preferred. Most preferred is about 35 to 39° C. The reaction time can be adjusted to the needs to obtain a suitable hydrogel. A suitable reaction time can be between 2 minutes and 45 hours, preferably 10 min to 24 hours.

The autoxidation of the hydrogel forming can be further supported by the step comprising adding an enzyme in the presence of an oxidant according to a another embodiment of the process. This accelerates the oxidation to form the hydrogel.

The enzyme can be a peroxidase. Such peroxidase can preferably be selected from the group consisting of horseradish peroxidase, human myeloperoxidase, lactoperoxidase, eosinophil peroxidase, thyroid peroxidase, prostaglandin H synthases, soybean peroxidase, hemin, hematin and microperoxidase-11. The oxidant can for example be a peroxide, such as hydrogen peroxide which is particularly preferred. The concentration of the peroxide and oxidant is not critical and can be chosen in known ranges. The enzyme can for instance be used in the amount of several units/mL, preferably 0.1 to 10 units/mL, more preferably 0.1 to 2 units/mL. The oxidant can be employed at mM level, preferably about 0 to 50 mM, more preferably 0.5 to 10 mM with 0.5 to 3 mM being most preferred.

Suitable hydrogels can be tuned by simply changing the enzyme concentrations or the amount of employed oxidant.

According to a fifth aspect of the invention, there is provided the use of the disclosed hydrogels for making biomedical products. Such biomedical products which can be mentioned include viscosupplements, anti-adhesion films or dermal fillers.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

DETAILED DESCRIPTION OF DRAWINGS

Figure 1:
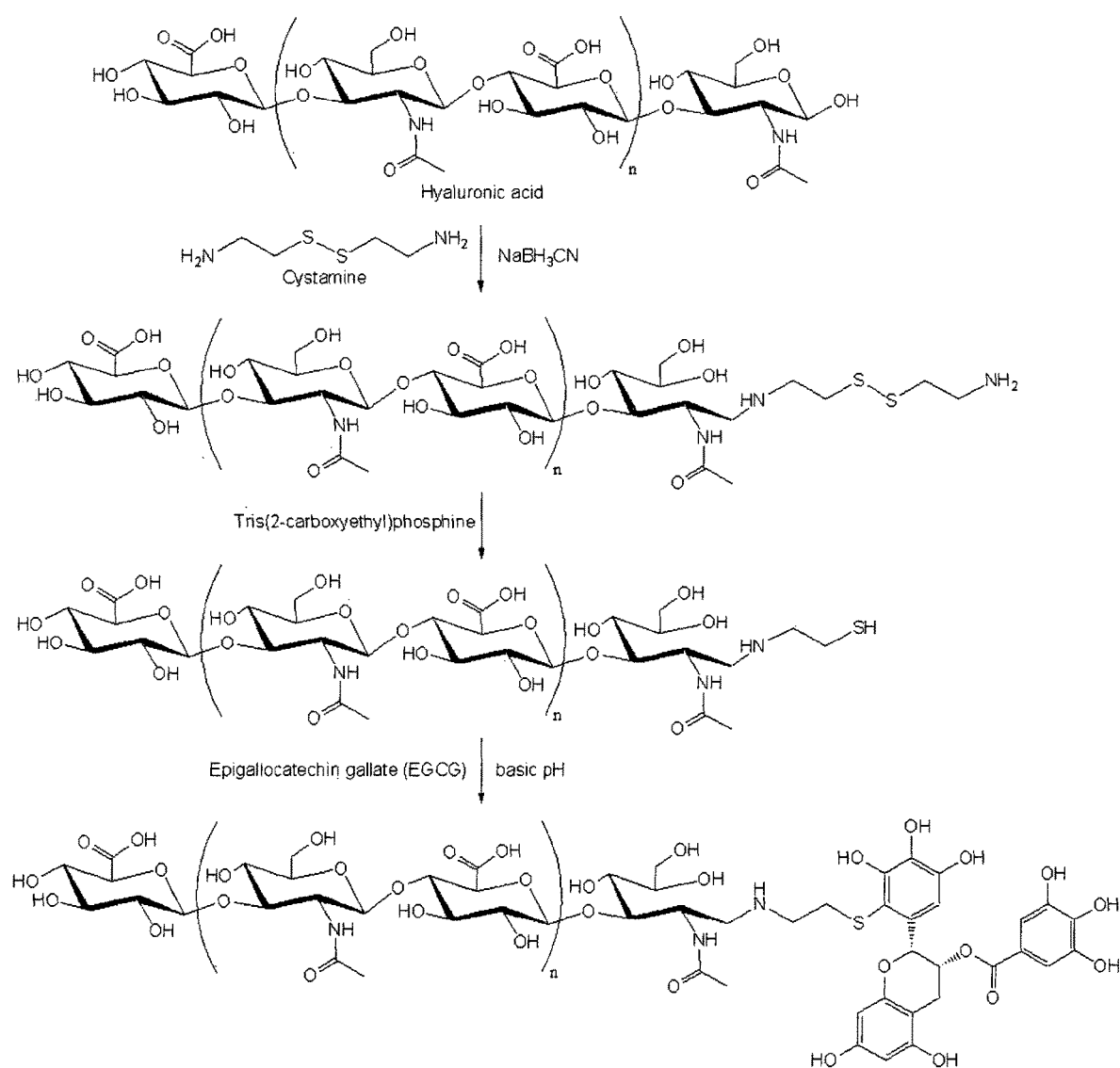
FIG. 1 shows the synthetic scheme of EGCG-terminated HA. A reducing end of HA molecule is modified with a thiol group by reductive amination and subsequent cleavage of disulphide bond. The resultant thiol-end modified HA is conjugated to EGCG at basic pH.

FIG. 1 shows a synthetic scheme of EGCG-terminated HA, in which a single EGCG molecule is attached at the terminal position of HA. It is known that most of polysaccharides (e.g., HA, dextran, cellulose, amylose, starch) contain only one reducing end having a cyclic hemiacetal group. For synthesis of EGCG-terminated HA, the native reducing end of HA molecule was first modified with cystamine by reductive amination. Subsequently, the disulphide bond in cystamine was cleaved by Tris(2-carboxyethyl)phosphine (TCEP) to generate a free thiol group at the terminal end of HA. The degree of thiolation determined by Ellman's assay was higher than 98%. The thiol end-modified HA was then incubated with excess amounts of EGCG at pH 7.4. As shown in the figure HA could be conjugated specifically to the B ring of EGCG at weak basic pH. It should be noted that the conjugation reaction was carried out in the presence of sodium pyruvate. The produced EGCG-terminated HA could be purified simply by dialysis against distilled water under nitrogen atmosphere.

Figure 2:
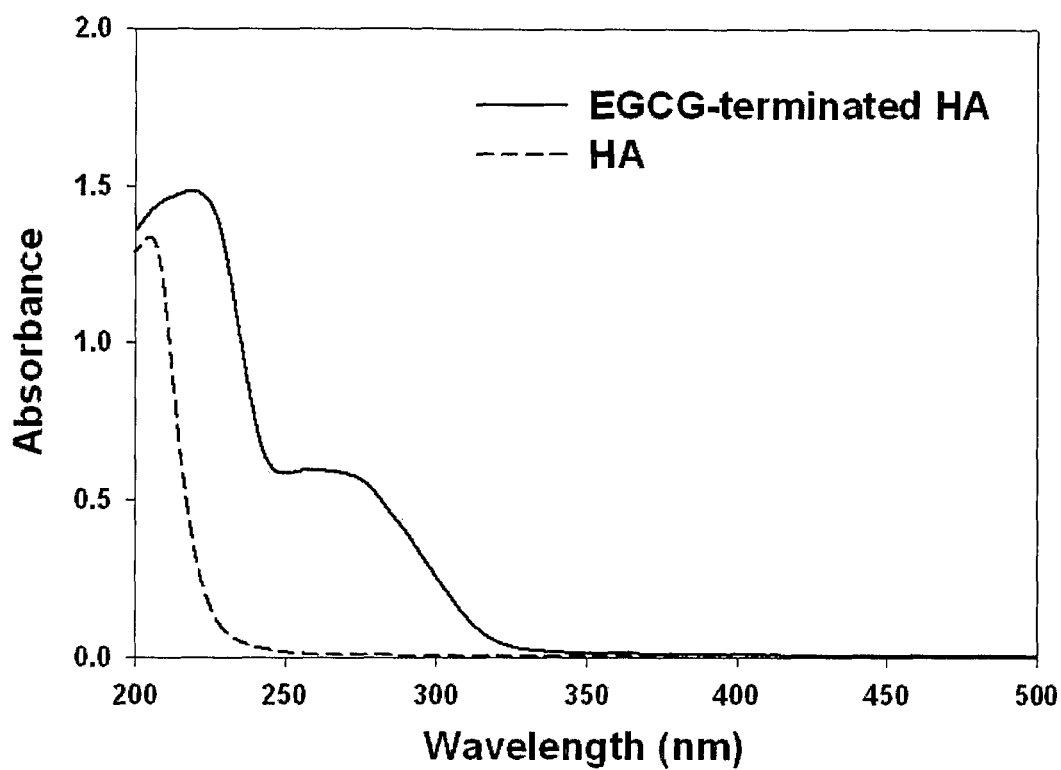
FIG. 2 shows the UV-visible spectra of HA and EGCG-terminated HA dissolved in distilled water at a concentration of 0.5 mg/mL.

FIG. 2 shows that EGCG-terminated HA had a characteristic UV absorption peak of EGCG at 274 nm. UV absorption band at 425 nm was not observed for EGCG-terminated HA, indicative of the absence of EGCG dimers and other oxidative products. The successful conjugation of EGCG was further confirmed by reverse-phase high-performance liquid chromatography (HPLC).

Figure 3:
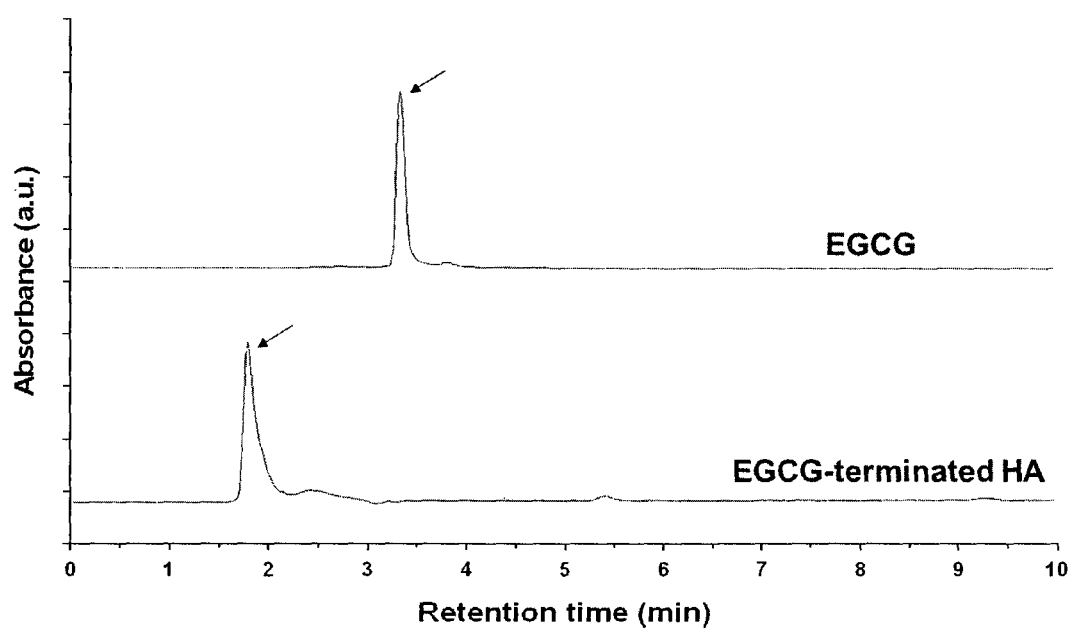
FIG. 3 shows the HPLC chromatograms of EGCG and EGCG-terminated HA. The upper and lower arrows indicate the peaks of EGCG and EGCG-terminated HA, respectively.

FIG. 3 shows that the EGCG-terminated HA was shown to be eluted out at a shorter retention time than EGCG. Notably, EGCG dimers were not detected in the HPLC chromatogram.

Figure 4:
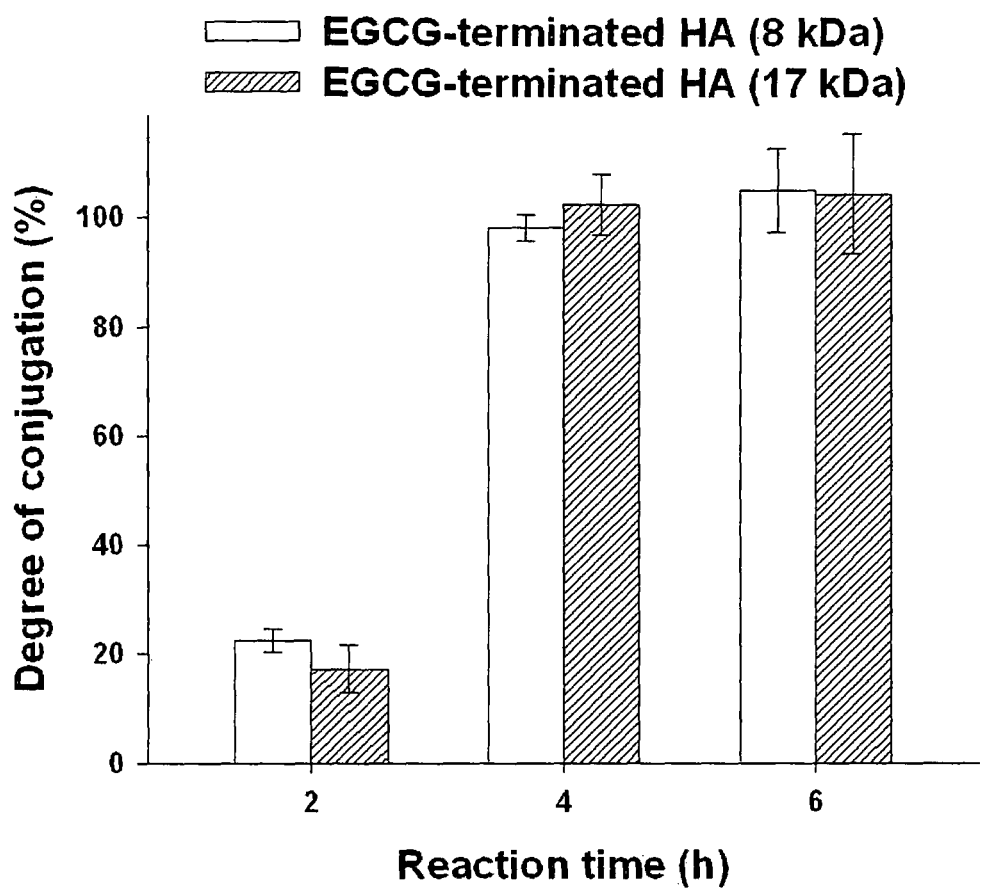
FIG. 4 shows the degree of conjugation of EGCG-terminated HA as a function of reaction time.

FIG. 4 shows that with increasing reaction times from 2 to 6 h, the degree of conjugation increased from 20 to 100%. The degree of conjugation was not dependent on the molecular weight of HA. From these results, the optimum reaction time was determined to be about 4 hours in this case.

Figure 5:
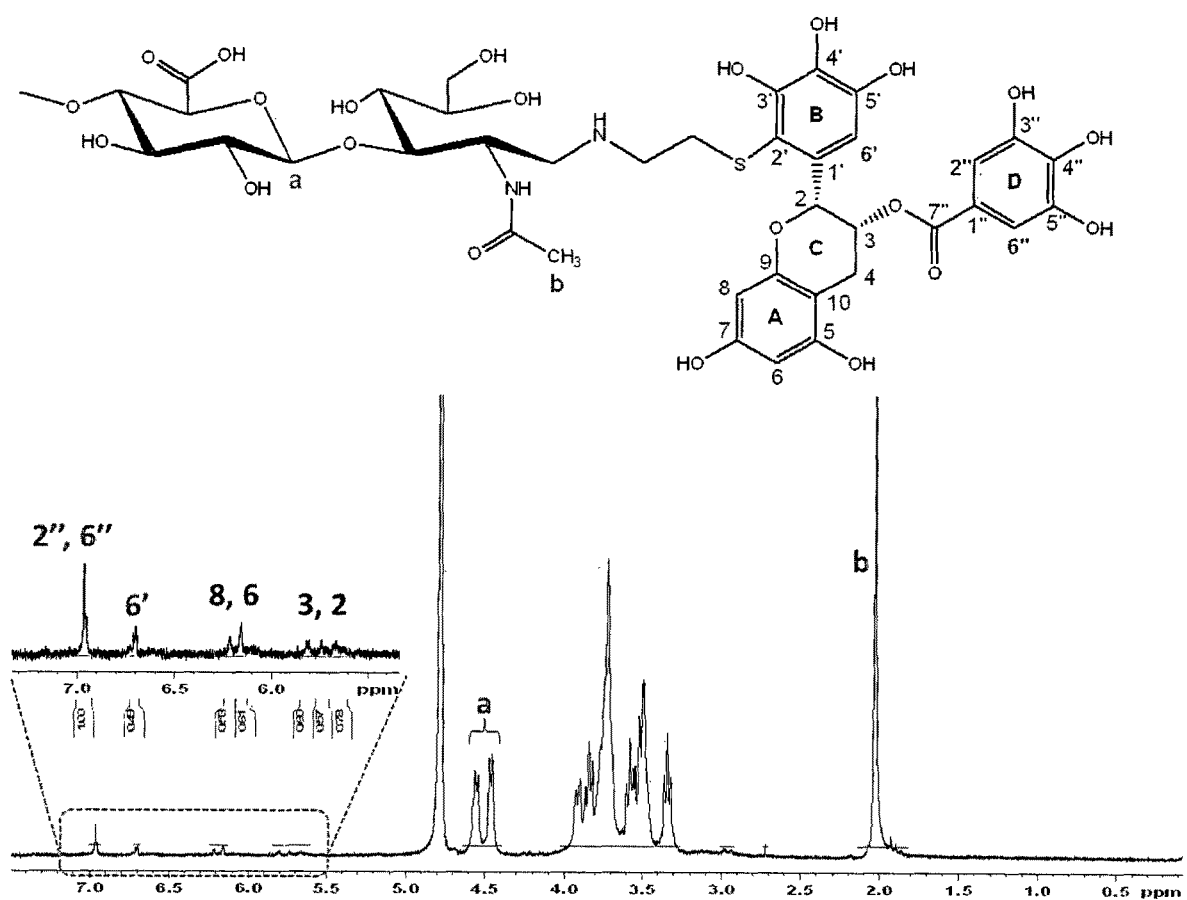
FIG. 5 shows the $^1$H NMR spectrum of EGCG-terminated HA with a molecular weight of 8 kDa.

FIG. 5 shows an evaluation of the structure of EGCG-terminated HA by $^1$H NMR spectroscopy. The $^1$H NMR spectrum showed proton signals for the A ring (H-6 and H-8 at δ=6.1-6.3), C ring (H-2 and H-3 at δ=5.60-5.85), and D ring (H-2" and H-6" at δ=6.95). Since the proton signals arising from the A, C, and D ring were similar to those of unmodified EGCG, it was conceivable that there structures were not involved in the conjugation reaction. In contrast, the proton signals for the B ring were apparently changed after the conjugation reaction. EGCG-terminated HA displayed a singlet signal for only one proton of B ring at δ=6.7 ppm, instead of a singlet signal for two protons of EGCG. This result can be explained by disappearance of one proton (H-2') through the attachment of thiol end-modified HA at the C2' position of the B ring. Furthermore, the proton signals of H-6' atom (δ=6.7) exhibited a downfield shift of 0.2 ppm as compared to that of unmodified EGCG. Taken together, these results demonstrated that only one HA molecule was attached at the C2' position of the B ring of EGCG in a site-specific manner.

According to the invention another type of HA-EGCG conjugates based on the site-specific conjugation method described above was synthesized to demonstrate the inventive concept.

Figure 6:
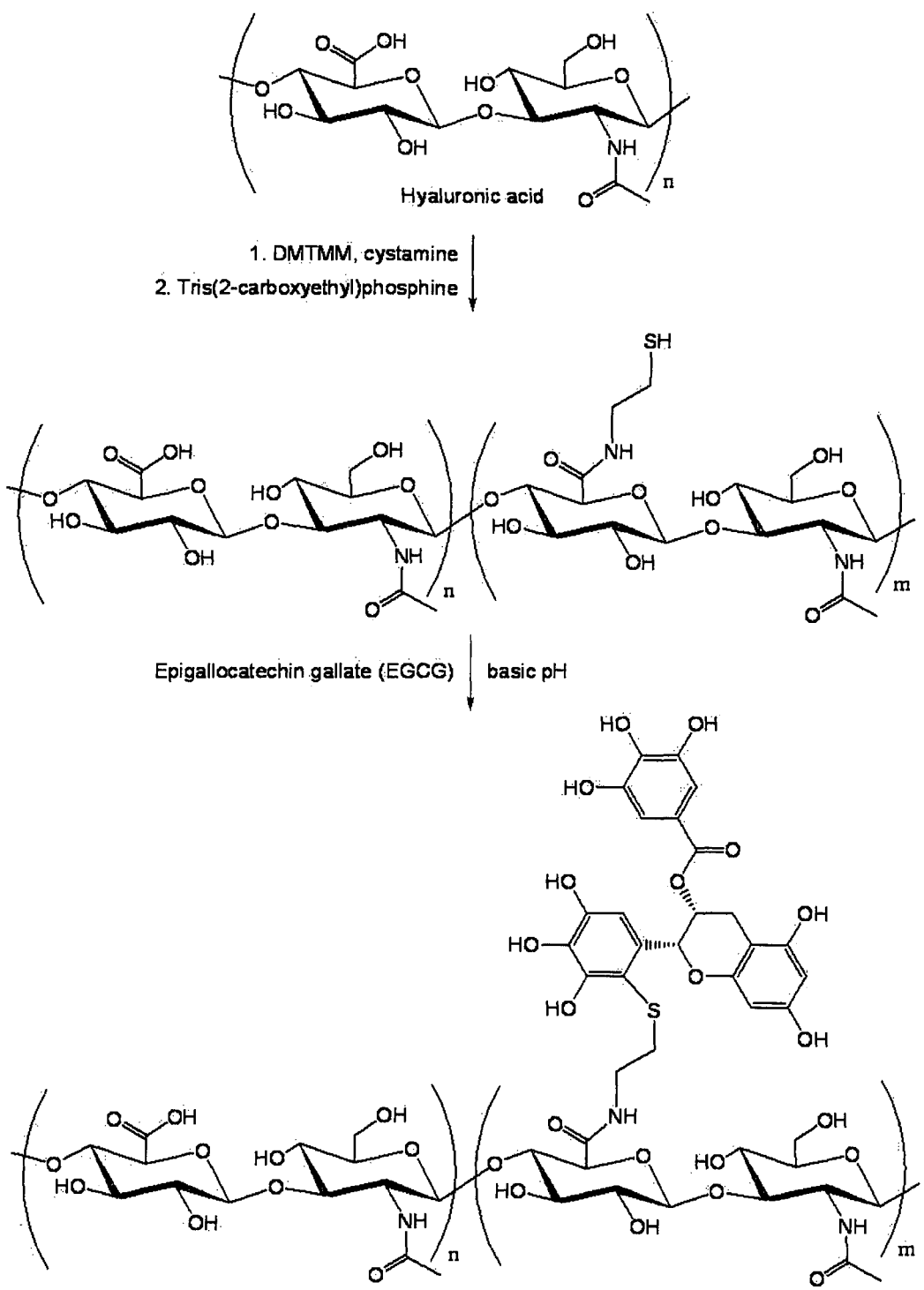
FIG. 6 shows the synthetic scheme of EGCG-grafted HA. Carboxyl groups in HA are modified with thiol groups by conjugation with cystamine molecules and subsequent cleavage of disulphide bond. The resultant thiol-functionalized HA is conjugated to EGCG at basic pH.

FIG. 6 shows a synthetic scheme of EGCG-grafted HA, which consists of multiple EGCG molecules connected to HA backbone. First, cystamine molecules were coupled to carboxyl groups of HA using a triazine-mediated reaction. Subsequently, the disulphide bond in cystamine was cleaved by TCEP to generate a free thiol group. The resultant HA-cysteamine conjugate has the degree of substitution (the number of thiol groups per 100 repeating disaccharide units) of 8.4, typically. The HA-cysteamine conjugate was then incubated with excess amounts of EGCG at pH 7.4 to allow conjugation of EGCG to the thiol groups. It is worth noting that sodium pyruvate was added to prevent the $H_2O_2$-mediated oxidation of free thiol groups. A small amount of DMSO was also added to increase the solubility of EGCG. After incubation for 24 hours at 25° C., the pH of the mixture was brought to 6 to stop the conjugation reaction. The produced EGCG-grafted HA was purified simply by dialysis against distilled water under nitrogen atmosphere.

Notably, the degree of substitution in HA-cysteamine conjugates was controlled by varying the molar ratio of the coupling agent (DMTMM) to the carboxyl group in HA. For example, the degree of substitution increased from 2.8 to 8.4 as the molar ratio of DMTMM to the carboxyl group was raised from 0.5:1 to 1.5:1. The use of HA-cysteamine conjugates with the degree of substitution of 5.7 and 8.4 resulted in the production of EGCG-grafted HA with the degree of substitution of 5.8 and 11, respectively. This result suggests that it is possible to tune the extent of EGCG conjugation simply by using HA-cysteamine conjugates with different degrees of substitution. Additionally, polyacrylic acid could be modified with cysteamine moieties using DMTMM in a controlled manner. For instance, the degree of substitution increased from 0.3 to 1.4 as the molar ratio of DMTMM to the carboxyl group was raised from 0.04:1 to 0.15:1. The use of polyacrylic acid-cysteamine conjugates with the degree of substitution of 1.0 and 1.4 resulted in the production of EGCG-grafted polyacrylic acid with the degree of substitution of 0.035 and 0.07, respectively.

Figure 7:
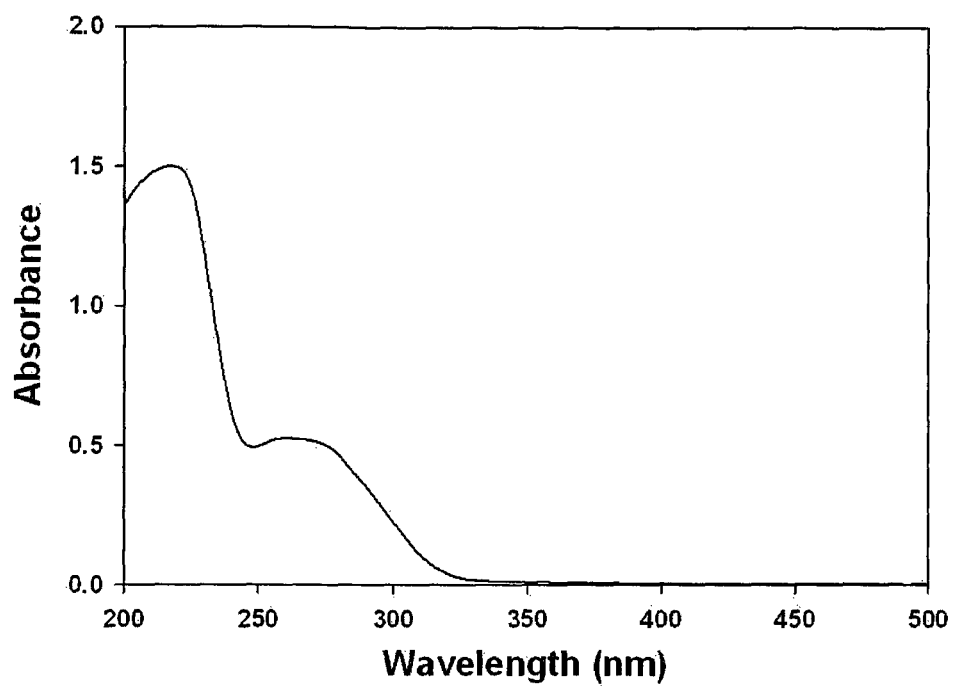
FIG. 7 shows the UV-visible spectrum of EGCG-grafted HA dissolved in distilled water at a concentration of 0.25 mg/mL.

FIG. 7 shows that the obtained EGCG-grafted HA displayed an UV absorption peak at 274 nm, indicative of the successful conjugation of EGCG. EGCG dimers and other oxidative products were not produced, as evident from the absence of UV absorption band at 425 nm.

Figure 8:
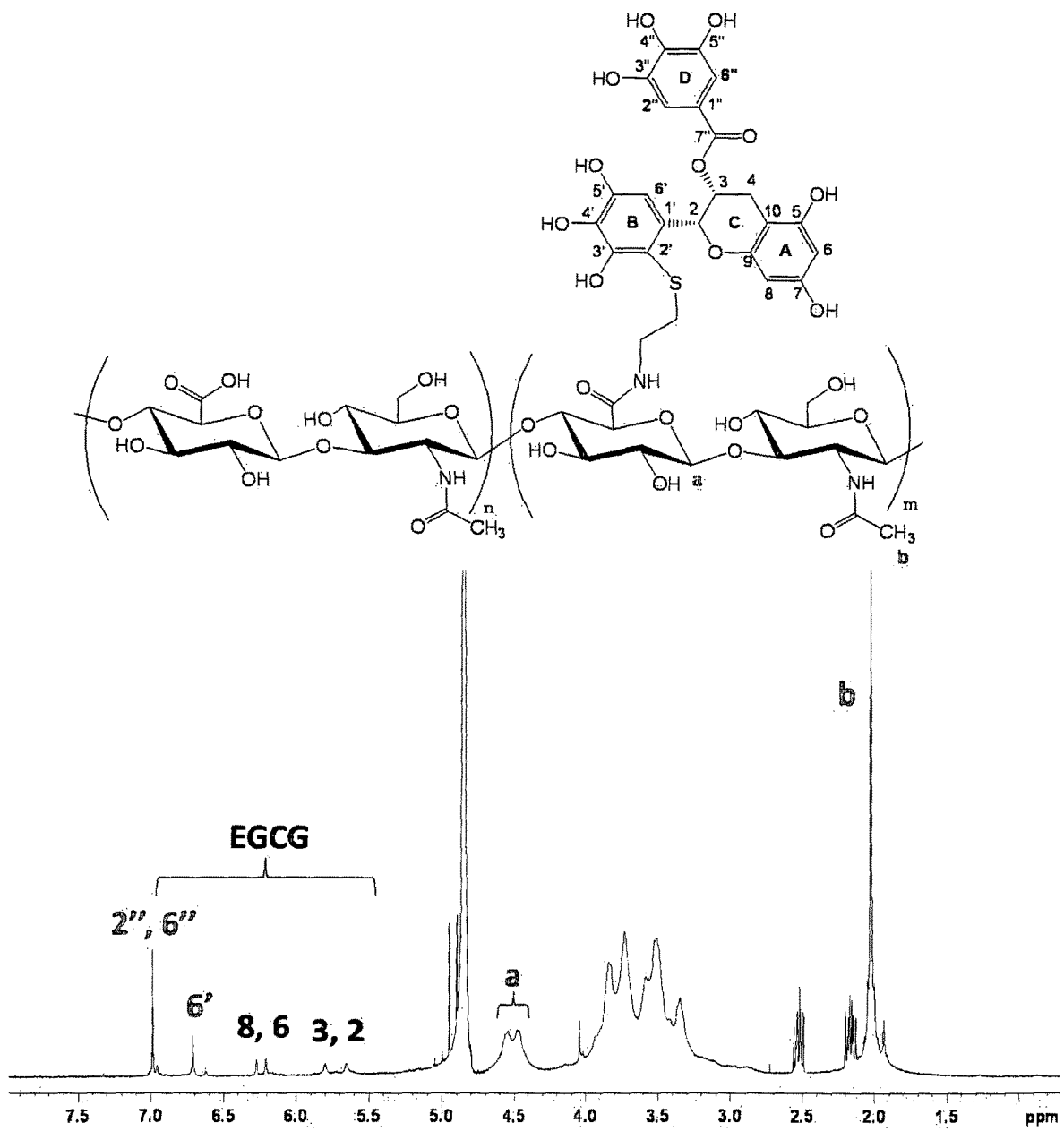
FIG. 8 shows the $^1$H NMR spectrum of EGCG-grafted HA with a molecular weight of 90 kDa.

FIG. 8 shows the $^1H$ NMR spectra of EGCG-grafted HA. The proton signals for the A ring (H-6 and H-8 at $\delta$=6.1-6.3), C ring (H-2 and H-3 at $\delta$=5.60-5.85) and D ring (H-2" and H-6" at $\delta$=6.98) were similar to those of unmodified EGCG, suggesting that there moieties did not undergo any change during the conjugation reaction. Importantly, the proton signals for the B ring were significantly shifted to $\delta$=6.7 ppm as compared to those of unmodified EGCG ($\delta$=6.5). Moreover, the NMR peak of B ring signals was shown to have half the area under the peak of the D ring signals, indicating one proton (H-2') disappeared from the B ring following the conjugation reaction. Hence the above results revealed that site-specific attachment of HA-cysteamine conjugates occurred solely at the C2' position of the B ring of EGCG.

The resulting EGCG-grafted HA is readily soluble in aqueous solution and can be utilized to form hydrogels through the crosslinking of the EGCG moieties. According to the invention HA-EGCG hydrogels can be produced by either autoxidation or enzymatic crosslinking reactions. To form HA-EGCG hydrogels via autoxidation, 2 wt % HA-EGCG solution was incubated at 37° C. and pH 7.4. The autoxidation-mediated formation of HA-EGCG hydrogels occurred slowly; the gelation time was approximately 2 h.

According to the invention it was found that the formation of HA-EGCG hydrogels could be accelerated by enzymatic crosslinking reactions using HRP.

Figure 9:
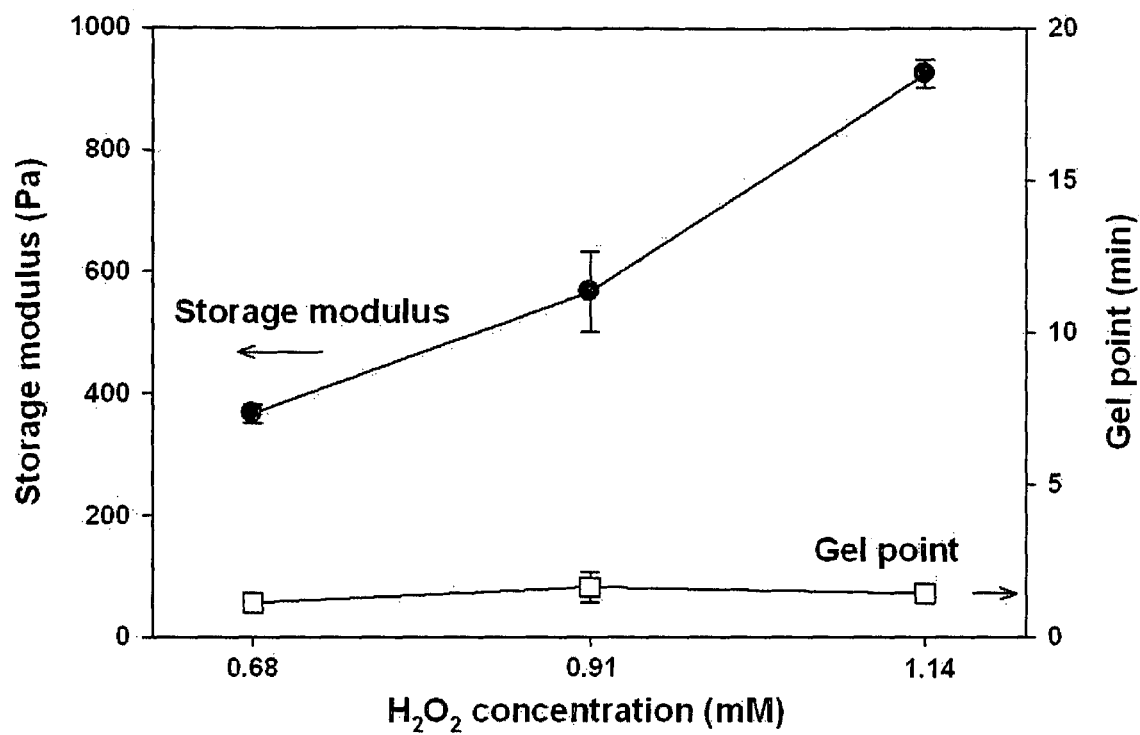
FIG. 9 shows the storage moduli and gel points of HA-EGCG hydrogels as a function of $H_2O_2$ concentration. The concentration of HRP was fixed at 0.16 units/mL.

FIG. 9 shows the gelation time was drastically reduced from 2 hours to 2 min when HRP was added at a concentration of 0.16 units/mL. This result shows that HRP accelerated the formation of EGCG dimers by catalyzing the oxidation of EGCG.

FIG. 9 shows the result of an examination of the storage moduli of HA-EGCG hydrogels at various $H_2O_2$ concentrations. The storage modulus increased gradually with increasing the $H_2O_2$ concentration. For example, the storage modulus increased from 366 Pa to 924 Pa as the $H_2O_2$ concentrations increased from 0.68 to 1.14 mM. Notably, the gel point of the hydrogels remained unchanged at about 0.2 min. This result indicates that the storage modulus of HA-EGCG hydrogels can be controlled without affecting their gelation rate.

Figure 10:
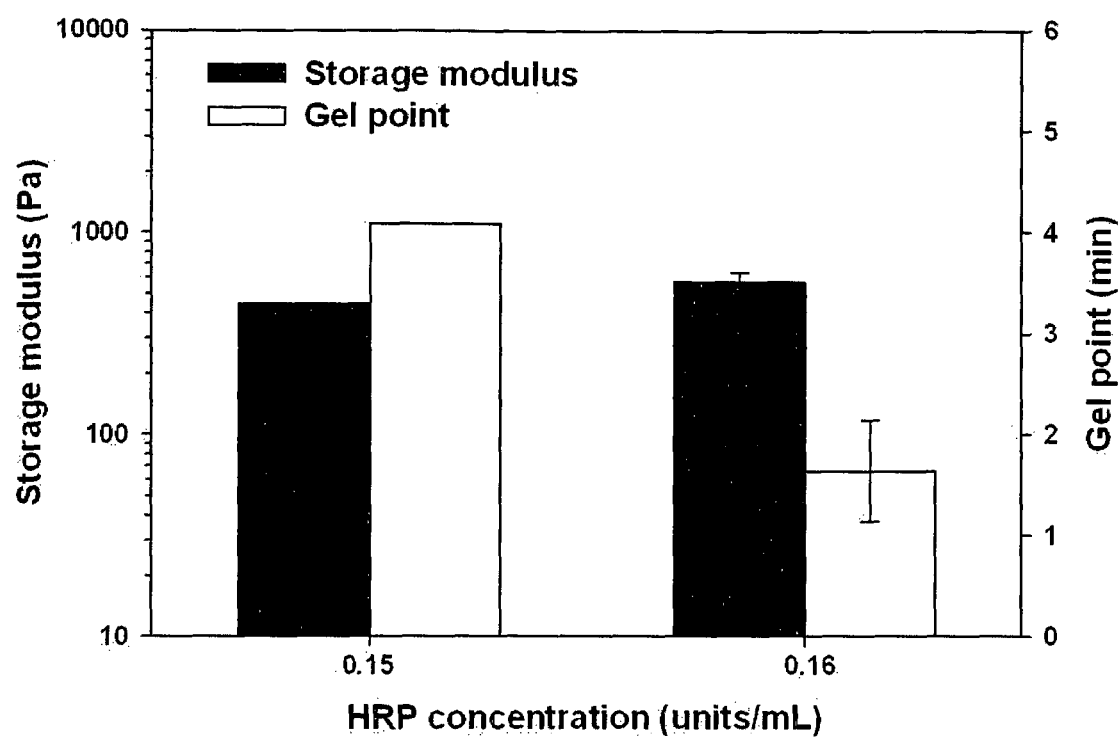
FIG. 10 shows the storage moduli and gel point of HA-EGCG hydrogels prepared with different concentrations of HRP. The concentration of $H_2O_2$ was fixed at 0.91 mmol/L.

FIG. 10 shows that the gelation rate became faster as the HRP concentration increased. The gel point of the hydrogels formed with 0.15 units/mL of HRP was 4.1 min, whereas that of the hydrogels formed with 0.16 units/mL of HRP was 1.6 min. Although the gelation rates were different, the formed hydrogels had similar storage moduli. These results show that the gelation rate of HA-EGCG hydrogels can be tuned by simply changing the HRP concentrations.

Figure 11:
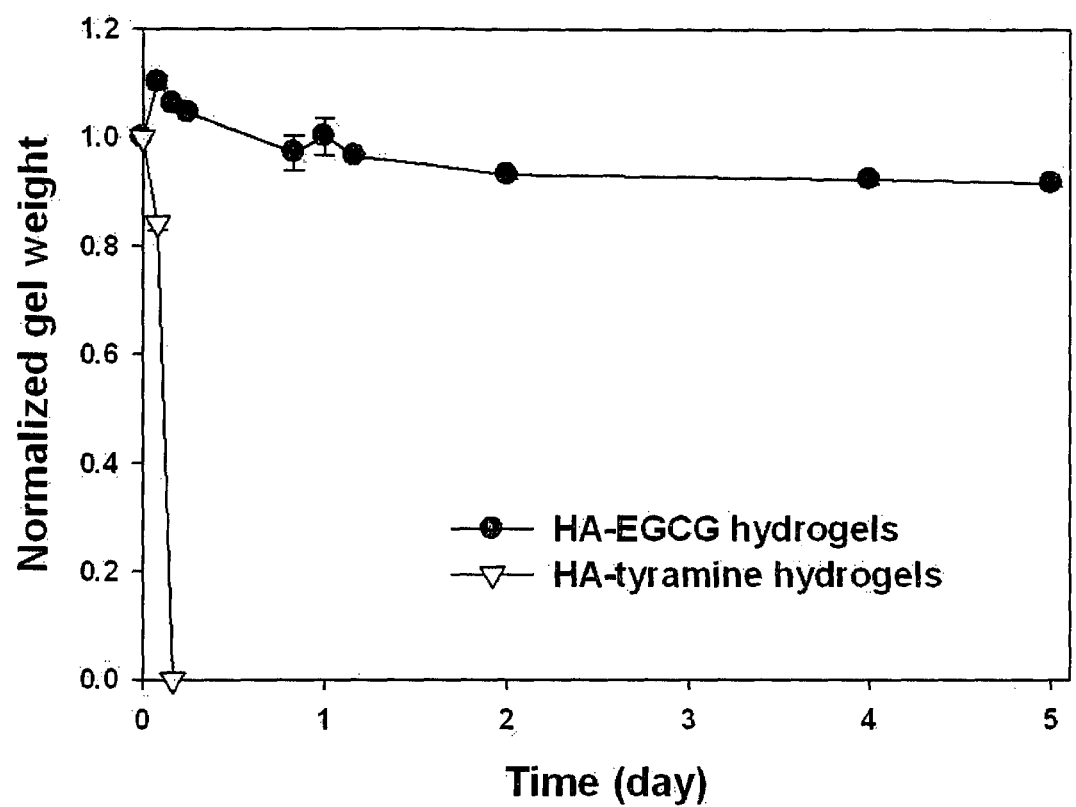
FIG. 11 shows the time course of change in the normalized weight of HA-EGCG and HA-tyramine hydrogels in the presence of 125 units/mL of hyaluronidase. Both hydrogels had the same storage moduli (1 kPa). HA-EGCG hydrogels were formed with 0.16 units/mL of HRP and 1.14 mmol/L of $H_2O_2$.

FIG. 11 shows the result of an investigation into the degradation profile of HA-EGCG hydrogels in the presence of 125 units/mL of hyaluronidase. For comparison, HA-tyramine hydrogels with the identical storage modulus (1 kPa) were prepared. In the human body, hyaluronidase exists in many organs, such as liver, spleen and kidney. Hyaluronidase causes a cleavage of glycosidic bond in the HA backbone. As expected, HA-tyramine hydrogels were quickly degraded by hyaluronidase within 6 hours. In contrast, HA-EGCG hydrogels exhibited only a marginal level of degradation (about 9%) for 5 days. EGCG moieties are responsible for the inhibition of hyaluronidase activity. These results suggest that HA-EGCG hydrogels would exhibit prolonged residence in the body over an extended period of time as compared to conventional HA hydrogels. It can therefore be expected that the HA-EGCG hydrogels with controllable gelation rate and mechanical strength can be utilized as an injectable scaffold for tissue engineering and controlled release of bioactive agents.

EXAMPLES

Synthesis/Preparation examples and non-limiting examples of the invention will be further described in greater detail by reference to specific Examples, which should not be construed as in any way limiting the scope of the invention.

Materials.

HA ($M_w$=8 and 17 kDa) was purchased from Lifecore Biomedical (Chaska, Minn.). HA ($M_w$=90 kDa) was kindly donated by JNC Corporation (Tokyo, Japan). (−)-Epigallocatechin-3-gallate (EGCG, >95% purity) was obtained from Kurita Water Industries (Tokyo, Japan). Polyacrylic acid (PAA, $M_w$=100 kDa), cystamine dihydrochloride, cysteamine hydrochloride, sodium tetraborate, sodium chloride (NaCl), sodium cyanoborohydride ($NaBH_3CN$), 4-(4,6-Dimethoxy-1,3,5-triazin-2-yl)-4-methylmorpholinium chloride (DMTMM), 5,5'-dithiobis (2-nitrobenzoic acid) (Ellman's reagent), and L-cysteine were purchased from Sigma-Aldrich (Minnesota, USA). Tris(2-carboxyethyl)phosphine hydrochloride (TCEP) was purchased from Tokyo Chemical Industry (Tokyo, Japan). Sodium pyruvate (100 mM solution) was obtained from Invitrogen (Carlsbad, Calif.). Horseradish peroxidase (HRP, 190 units/mg) was purchased from Wako Pure Chemical Industries (Osaka, Japan). Hydrogen peroxide ($H_2O_2$) was obtained from Lancaster. All other chemicals were of analytical grade.

Synthesis Example 1

Synthesis of EGCG-Terminated HA

HA (8 and 17 kDa) was first modified with thiol group at the reducing end according to the previous report with minor modifications (Lee, H.; Lee, K.; Kim, I. K.; Park, T. G. Synthesis, characterization, and in vivo diagnostic applications of hyaluronic acid immobilized gold nanoprobes. *Biomaterials* 29:4709-4718; 2008). Typically, HA (8 kDa, 500 mg) and cystamine dihydrochloride (1.2 g, 10.6 mmol) were dissolved in 30 mL of 0.1 M borate buffer (pH 8.5) containing 0.4 M NaCl. The reaction mixture was stirred for 2 h at 25° C. To this solution, NaBH$_3$CN (628 mg, 10 mmol) dissolved in 20 mL of 0.1 M borate buffer (pH 8.5) was slowly added. The mixture was incubated at 37° C. for 5 days while stirring. Then, 15 mL of 0.5 M TCEP solution (pH 7) was added and stirred for 2 h at 25° C. to generate free thiol groups. The resulting mixture was transferred to dialysis tubes with a molecular weight cutoff of 1,000 Da. The tubes were dialyzed against 0.1 M NaCl solution for 2 days, 25% ethanol for 1 day, and distilled water for 2 days under nitrogen atmosphere. The purified solution was lyophilized to obtain thiol end-modified HA. After lyophilization, the final product was kept at −20° C. in the dark. The amount of free thiol groups in HA was determined by Ellman's assay using L-cysteine as a standard (Ellman, G. L. A colorimetric method for determining low concentrations of mercaptans. *Arch Biochem Biophys.* 74:443-50; 1958). The efficiency of thiol end-modification of HA was higher than 98%, as determined by Ellman's assay. Yield: 93%.

For conjugation reaction, EGCG (440 mg, 0.96 mmol) was dissolved in 60 mL of 10 mM phosphate-buffered saline (PBS, pH 7.4) containing 2 mM of sodium pyruvate. Thiol end-modified HA (100 mg, 0.012 mmol) was dissolved in 10 mL of PBS solution containing 2 mM of sodium pyruvate. Then, the solution was added dropwise to a stirred solution of EGCG. The mixture was stirred for 4 h at 25° C. The resultant solution was transferred to dialysis tubes with a molecular weight cutoff of 2,000 Da. The tubes were extensively dialyzed against nitrogen-purged distilled water. The purified solution was lyophilized to obtain EGCG-terminated HA. The structure of the product was confirmed by $^1$H NMR spectroscopy. Yield: 93%. $^1$H NMR (D$_2$O): δ 2.1 (s, —C=OCH$_3$ from HA), 2.9-3.0 (d, H-4 of C ring), 3.3-4.0 (m, protons of HA), 4.45 and 4.55 (d, HA anomeric proton), 5.60-5.85 (s, H-2 and H-3 of C ring), 6.1-6.3 (s, H-6 and H-8 of A ring), 6.7 (s, H-6' of B ring), 6.95 (s, H-2" and H-6" of D ring).

Synthesis Example 2

Synthesis of EGCG-Grafted HA

Thiolated HA derivatives with different degrees of thiolation were synthesized by modifying carboxyl groups in HA backbone with thiol groups. Typically, 1 g of HA (90 kDa, 2.5 mmol —COOH) was dissolved in 100 mL of PBS solution (pH 7.4). To this solution 1.037 g (3.75 mmol) of DMTMM was added. Cystamine dihydrochloride (844.5 mg, 3.75 mmol) dissolved in 10 mL of PBS solution (pH 7.4) was then added to initiate the conjugation reaction. The reaction mixture was stirred for 24 hours at 25° C. Then, 15 mL of 0.5 M TCEP solution (pH 7) was added and stirred for 1 h at 25° C. to generate free thiol groups. The solution was transferred to dialysis tubes with a molecular weight cut-off of 3,500 Da. The tubes were dialyzed against 0.1 M NaCl solution for 2 days, 25% ethanol for 1 day and distilled water for 2 days, successively. All dialysis was performed under nitrogen atmosphere. The purified solution was lyophilized to obtain HA-cysteamine conjugate (0.87 g). The degree of substitution (DS) is defined as the number of substituents per 100 repeating disaccharide units in HA. DS was determined to be 8.4 by Ellman's assay.

The dried HA-cysteamine conjugate (0.5 g, 105 μmol—SH) was dissolved in 70 mL of PBS solution (pH 7.4). To this solution, 2.5 mL of 0.5 M TCEP solution (pH 7) was added. EGCG (1.547 g, 3.375 mmol) was dissolved in a premixed solvent (23 mL of 0.1 M PBS solution (pH 7.4), 5 mL of DMSO, and 2 mL of 100 mM sodium pyruvate) under nitrogen atmosphere. This solution was then added to a conjugate, wherein said polymer is conjugated to said avonoid via a thiol linker.
solution. The reaction mixture was stirred for 24 h at 25° C. Then, the pH of the mixture was brought to 6 by adding 10% acetic acid before transferring the solution to dialysis tubes with a molecular weight cut-off of 3,500 Da. The tubes were dialyzed against distilled water for 5 days under nitrogen atmosphere. The purified solution was lyophilized to obtain EGCG-grafted HA (0.48 g). DS was determined by measuring the absorbance of EGCG at 274 nm. DS was 11. The structure of the product was confirmed by $^1$H NMR spectroscopy. $^1$H NMR (D$_2$O): δ 2.0 (s, —C=OCH$_3$ from HA), 3.3-4.0 (m, protons of HA), 4.51 and 4.54 (d, HA anomeric proton), 5.60-5.85 (s, H-2 and H-3 of C ring), 6.1-6.3 (s, H-6 and H-8 of A ring), 6.7 (s, H-6' of B ring), 6.98 (s, H-2" and H-6" of D ring).

Synthesis Example 3

Synthesis of EGCG-Grafted PAA

Thiolated PAA derivatives with different degrees of thiolation were synthesized by modifying carboxyl groups in PAA backbone with thiol groups. Typically, 10 g of PAA (90 kDa, 138.8 mmol —COOH) was dissolved in 250 mL of deionized water. The pH of the solution was brought to 5 by adding 10 M NaOH solution. To this solution 5.8 g (21 mmol) of DMTMM was added. Cysteamine dihydrochloride (2389 mg, 21 mmol) was then added to initiate the conjugation reaction. The reaction mixture was stirred for 24 hours at 25° C. The solution was transferred to dialysis tubes with a molecular weight cut-off of 3,500 Da. The tubes were dialyzed against 0.1 M NaCl solution for 1 day under nitrogen atmosphere. Then, TCEP (3 g, 10.5 mmol) dissolved in 5 mL of water (pH 5) was added and reacted for 1 h at 25° C. to generate free thiol groups. Then, the solution was transferred to dialysis tubes with a molecular weight cut-off of 3,500 Da. The tubes were dialyzed against 0.1 M NaCl solution for 2 days, 25% ethanol for 1 day and distilled water for 2 days, successively. All dialysis was performed under nitrogen atmosphere. The purified solution was lyophilized to obtain PAA-cysteamine conjugate (8.7 g). The degree of substitution (DS) is defined as the number of substituents per 100 repeating units in PAA. DS was determined to be 1.4 by Ellman's assay.

The dried PAA-cysteamine conjugate (0.5 g, 100 μmol —SH) was dissolved in 70 mL of PBS solution (pH 7.4). To this solution, 1.5 mL of 0.5 M TCEP solution (pH 7) was added. EGCG (1.547 g, 3.375 mmol) was dissolved in a premixed solvent (23 mL of 0.1 M PBS solution (pH 7.4), 5 mL of DMSO, and 2 mL of 100 mM sodium pyruvate) under nitrogen atmosphere. This solution was then added to a stirred solution of PAA-cysteamine conjugate. The pH of the mixture was brought to 7.4 by adding 10 M NaOH solution. The reaction mixture was stirred for 24 h at 25° C. Then, the pH of the mixture was brought to 6 by adding 10% acetic acid before transferring the solution to dialysis tubes with a molecular weight cut-off of 3,500 Da. The tubes were dialyzed against distilled water for 5 days under nitrogen atmosphere. The purified solution was lyophilized to obtain EGCG-grafted PAA (0.48 g). DS was determined by measuring the absorbance of EGCG at 274 nm. DS was 0.07.

Synthesis Example 4

Characterization of HA-EGCG Conjugates

UV-visible spectra of HA-EGCG conjugates were measured on a Hitachi U-2810 spectrophotometer. The extent of EGCG conjugation was determined by measuring the absorbance of EGCG at 274 nm. Reverse-phase high-performance liquid chromatography (HPLC) was carried out using a Waters 2695 separations module equipped with a Spirit™ C18 organic column (5 μm, 4.6×250 mm i.d., AAPPTec). EGCG and HA-EGCG conjugates were dissolved in deionized water at a concentration of 1 mg/mL. The samples were eluted with a solvent mixture of 1% acetic acid in water and 1% acetic acid in acetonitrile (6:4, v/v) at a flow rate of 1.0 mL/min at 25° C. The elution profiles were monitored at 280 nm.

Synthesis Example 5

Formation of HA-EGCG Hydrogels Through Autoxidation

A stock solution of HA-EGCG conjugate (90 kDa) was prepared by dissolving the conjugate in distilled water at a concentration of 22.5 mg/mL at 25° C. Typically, 4 mL of the stock solution was diluted with 0.5 mL of 90 mM PBS solution (final ionic strength: 0.16 M, pH 7.4) to give a final HA-EGCG concentration of 20 mg/mL. To form HA-EGCG hydrogels by autoxidation, 270 μL of HA-EGCG solution (20 mg/mL) was incubated at 37° C. The gelation time was determined by the vial tilting method. The gel state was regarded when no obvious flowing motion could be observed within a minute after inversion of the vial containing a hydrogel.

Synthesis Example 6

Formation of HA-EGCG Hydrogels by HRP-Mediated Crosslinking Reaction

HA-EGCG solution (20 mg/mL) was prepared in PBS solution (final ionic strength: 0.16 M, pH 7.4) as described above. To produce hydrogels, 270 μL of the HA-EGCG solution was mixed with 3 μL of HRP solution with different concentrations (final HRP concentrations: 0.15 and 0.16 units/mL). Subsequently, 3 μL of $H_2O_2$ solution was added at final concentrations ranging from 0.68 to 1.14 mM, and mixed homogenously by gentle vortex. Gelation was allowed to proceed at 37° C. The gelation time was determined by the vial tilting method. The gel state was regarded when no obvious flowing motion could be observed within a minute after inversion of the vial containing a hydrogel.

Rheological Characterization of HA-EGCG Hydrogels.

For rheological characterization, 270 μL of HA-EGCG solution (20 mg/mL) was mixed with 3 μL of HRP solution with different concentrations (final HRP concentrations: 0.15 and 0.16 units/mL). Subsequently, 3 μL of $H_2O_2$ solution was added at final concentrations ranging from 0.68 to 1.14 mM. The mixture was immediately vortexed and 210 μL of which was applied to the bottom plate of a HAKKE Rheoscope 1 rheometer (Karlsruhe, Germany). Rheological measurement was carried out at 37° C. in the dynamic oscillatory mode with a constant deformation of 1% and a frequency of 1 Hz, using a cone and plate geometry of 3.5 cm diameter and 0.949° cone angle. The evolution of storage modulus (G') and loss modulus (G") was monitored as a function of time. The measurement was carried out until G' reached a plateau. The time at which the crossover of G' and G" occurred was recorded as the gel point.

Enzymatic Degradation of HA-EGCG and HA-Tyramine Hydrogels.

For degradation analysis, 270 μL of HA-EGCG solution (20 mg/mL) was mixed with 3 μL each of HRP and $H_2O_2$ solution. The final concentration of HRP and $H_2O_2$ used to form HA-EGCG hydrogels was 0.16 units/mL and 1.14 mM, respectively. The mixture was immediately vortexed and 210 μL of which was injected between two parallel glass plates clamped together with 1.5 mm spacing. Gelation was allowed to proceed for 2 h at 37° C. on an orbital shaker at 50 rpm. For comparison, HA-tyramine hydrogels with the storage moduli of 1 kPa were prepared according to the methods reported previously (Lee, F.; Chung, J. E.; Kurisawa, M. An injectable enzymatically crosslinked hyaluronic acid-tyramine hydrogel system with independent tuning of mechanical strength and gelation rate. *Soft Matter* 4, 880-887; 2008). HA-EGCG and HA-tyramine hydrogels were immersed in 20 mL of PBS solution (pH 7.4) containing 125 units/mL of bovine testicular hyaluronidase, and then incubated at 37° C. in a shaking incubator. At the indicated time points, the hydrogels were removed from the solution and weighed out. The normalized gel weight was determined from the initial weight and the residual weight of the hydrogels after degradation according to the following equation: normalized gel weight=Wt/W0, where W0 is the initial weight of the hydrogels and Wt is the residual weight of the hydrogels after degradation.

Applications

The disclosed flavonoid-polymer conjugates increase the bioavailability and stability of the flavonoids.

Advantageously, they can be used to make flavonoids available in applications which require a higher lifetime of the molecule to make it effective in biomedical applications.

More advantageously, the hydrogels can be easily formed from the flavonoid-polymer conjugates. These hydrogels may have biomedical applications.

Such application areas include the making of non-adhesive films for tissue coverings as well as injectable gels. Typical applications that can be mentioned are viscosupplements or dermal fillers.

Further advantageously, the gels can be varied according to the inventive processes for making them and the conjugates. Therefore the invention opens up a new class of applications where different characteristics are needed.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A polymer-flavonoid conjugate, wherein said polymer is conjugated specifically at the C2' position of the B ring of said flavonoid via a thiol linker and the polymer is selected from the group consisting of polysaccharides, synthetic polymers comprising carboxylic acid monomers, and mixtures of said polysaccharides and said synthetic polymers comprising carboxylic acid monomers, wherein said thiol linker is derived from a thiol moiety bound to said polymer, and wherein said thiol moiety consists of an amine and an alkyl group.

2. The polymer-flavonoid conjugate according to claim 1, wherein said polysaccharide is selected from the group consisting of hyaluronic acid, alginate, gellangum, pectin andxanthan gum.

3. The polymer-flavonoid conjugate according to claim 1, wherein said synthetic polymers comprising the carboxylic acid monomers are selected from the group consisting of polyacrylic acid, polyglycolic acid, poly(3-hydroxypropionic acid), polylactic acid, poly(lactic-co-glycolic acid), poly(methacrylic acid), poly(sebacic acid), and combinations thereof.

4. The polymer-flavonoid conjugate according to claim 1, wherein said polymer is selected from polyacrylic acid or hyaluronic acid.

5. The polymer-flavonoid conjugate according to claim 1, wherein said alkyl group is ethyl group.

6. The polymer-flavonoid conjugate according to claim 1, wherein said polymer-flavonoid conjugate is a Hyaluronic acid-EGCG conjugate which is selected from the group consisting of:

Formula (I)

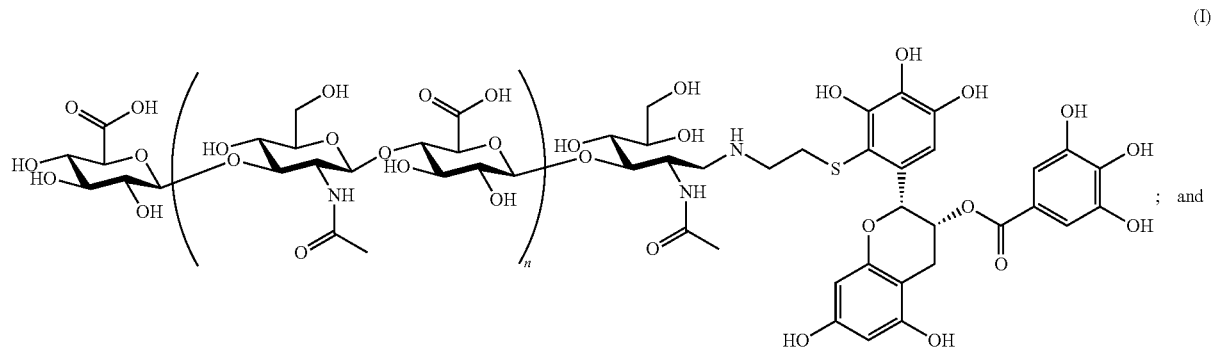

; and

Formula (II)

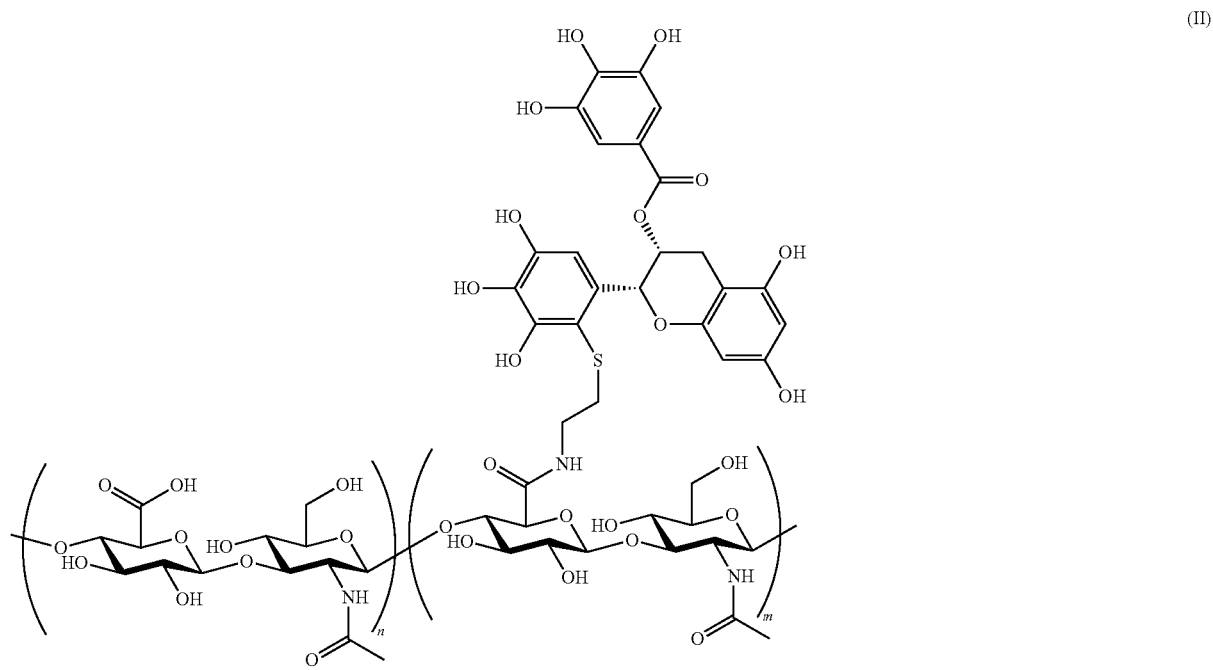

wherein:
each n is independently an integer from 1 to 15,000 inclusive; and each m is independently an integer from 1 to 15,000 inclusive.

7. A process for forming a polymer-flavonoid conjugate, wherein said polymer is conjugated specifically at the C2' position of the B ring of said flavonoid via a thiol linker and the polymer is selected from the group consisting of polysaccharides, synthetic polymers comprising carboxylic acid monomers, and mixtures of said polysaccharides and synthetic polymers comprising carboxylic acid monomers, wherein said thiol linker is derived from a thiol moiety bound to said polymer, and wherein said thiol moiety consists of an amine and an alkyl group, comprising the operation of conjugating said polymer specifically at the C2' position of the B ring of said flavonoid via nucleophilic addition under basic conditions, wherein said polymer has been modified with a free thiol group.

8. The process according to claim 7, further comprising:
(a) linking a thiol or disulphide-containing compound to said polymer in the presence of a reducing agent; and
(b) cleaving said disulphide-containing compound at the disulphide bond to thereby form said polymer bearing a terminal thiol group.

9. The process according to claim 8, wherein said reducing agent is selected from the group consisting of sodium cyanoborohydride, sodium borohydride, sodium triacetoxyborohydride and lithium aluminium hydride.

10. The process according to claim 7, further comprising the operation of coupling a thiol or disulphide-containing compound to said polymer in the presence of a coupling agent.

11. The process according to claim 7, further comprising the operation of adding a scavenging agent in the nucleophilic addition.

12. A hydrogel obtained from a polymer-flavonoid conjugate, wherein said polymer is conjugated specifically at the C2' position of the B ring of said flavonoid via a thiol linker and the polymer is selected from the group consisting of polysaccharides, synthetic polymers comprising carboxylic acid monomers, and mixtures of said polysaccharides and said synthetic polymers comprising carboxylic acid monomers, wherein said thiol linker is derived from a thiol moiety bound to said polymer, and wherein said thiol moiety consists of an amine and an alkyl group.

13. The hydrogel according to claim 12, wherein said polymer-flavonoid conjugate is of the Formula (II)

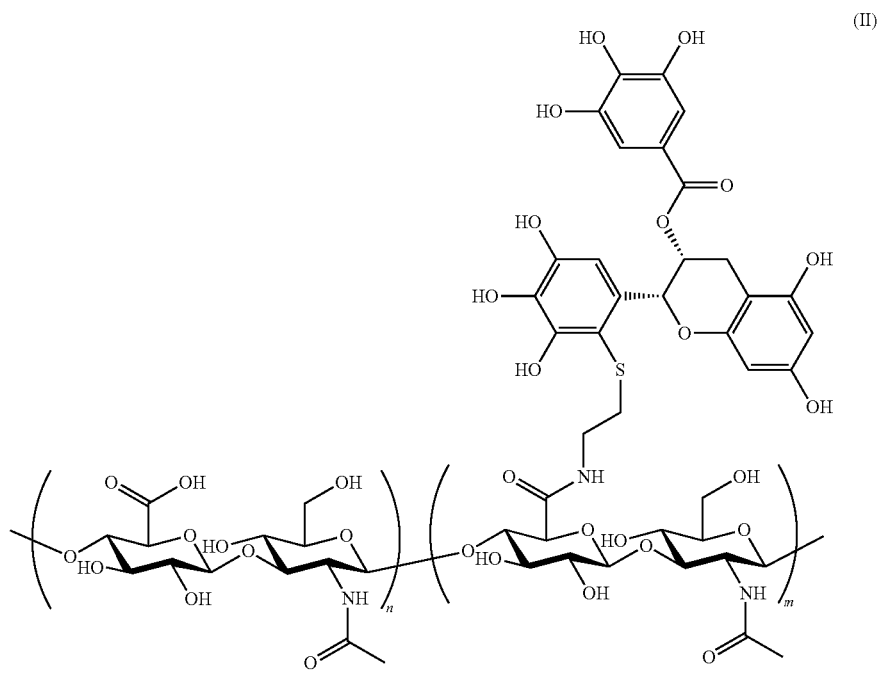

and has a degree of conjugation from 0.01 to 40%;
wherein:
each n is independently an integer from 1 to 15,000 inclusive; and each m is independently an integer from 1 to 15,000 inclusive.

14. A process for forming a hydrogel comprising the operation of cross-linking a polymer-flavonoid conjugate via autoxidation under basic conditions, wherein said polymer is conjugated specifically at the C2' position of the B ring of said flavonoid via a thiol linker and the polymer is selected from the group consisting of polysaccharides, synthetic polymers comprising carboxylic acid monomers, and mixtures of said polysaccharides and said polymers comprising carboxylic acid monomers, wherein said thiol linker is derived from a thiol moiety bound to said polymer, and wherein said thiol moiety consists of an amine and an alkyl group.

15. The process according to claim 14, wherein said cross-linking operation further comprises the operation of adding an enzyme in the presence of an oxidant.

16. A biomedical product selected from a viscosupplement, anti-adhesion film or dermal filler, wherein the biomedical product comprises a hydrogel obtained from a polymer-flavonoid conjugate, wherein said polymer is conjugated specifically at the C2' position of the B ring of said flavonoid via a thiol linker and the polymer is selected from the group consisting of polysaccharides, synthetic polymers comprising carboxylic acid monomers, and mixtures of said polysaccharides and said synthetic polymers comprising carboxylic acid monomers, wherein said thiol linker is derived from a thiol moiety bound to said polymer, and wherein said thiol moiety consists of an amine and an alkyl group.

* * * * *